United States Patent
Langenau et al.

(10) Patent No.: US 10,543,287 B2
(45) Date of Patent: Jan. 28, 2020

(54) IMMUNE-COMPROMISED ZEBRAFISH

(71) Applicant: The General Hospital Corporation, Boston, MA (US)

(72) Inventors: David M. Langenau, Stoneham, MA (US); Jessica Susanne Blackburn, Chelmsford, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/903,940

(22) PCT Filed: Jul. 9, 2014

(86) PCT No.: PCT/US2014/045963
§ 371 (c)(1),
(2) Date: Jan. 8, 2016

(87) PCT Pub. No.: WO2015/006455
PCT Pub. Date: Jan. 15, 2015

(65) Prior Publication Data
US 2016/0166713 A1 Jun. 16, 2016

Related U.S. Application Data

(60) Provisional application No. 61/844,694, filed on Jul. 10, 2013.

(51) Int. Cl.
| | | |
|---|---|---|
| G01N 33/00 | (2006.01) | |
| A01K 67/027 | (2006.01) | |
| A61K 49/00 | (2006.01) | |

(52) U.S. Cl.
CPC ...... *A61K 49/0008* (2013.01); *A01K 67/0271* (2013.01); *A01K 2207/12* (2013.01); *A01K 2227/40* (2013.01); *A01K 2267/0331* (2013.01)

(58) Field of Classification Search
CPC .............. A61K 49/008; A01K 67/0271; A01K 67/0276; G01N 33/00
USPC ...................................................... 800/20, 3
See application file for complete search history.

(56) References Cited

U.S. PATENT DOCUMENTS

| 7,408,095 B2 | 8/2008 | Serbedzija et al. |
| 7,525,011 B2 | 4/2009 | Look et al. |
| 9,314,005 B2 * | 4/2016 | Ostertag ............ A01K 67/0276 |

FOREIGN PATENT DOCUMENTS

| WO | WO 2011/002988 | 1/2011 |

OTHER PUBLICATIONS

Tang (2014, Nature Methods, 11:821-824).*
Ito (2002 Blood 100:3175-3182).*
Teittinen (Jun. 2012, 36:1082-1088).*
Cade et al., "Highly efficient generation of heritable zebrafish gene mutations using homo- and heterodimeric TALENs," Nucleic Acids Research, 2012, 40(16):8001-8010.
Doyon et al., "Heritable Targeted Gene Disruption in Zebrafish Using Designed Zinc Finger Nucleases," Nat. Biotechnol., Jun. 2008, 26(6):702-708.
Foley et al., "Rapid Mutation of Endogenous Zebrafish Genes Using Zinc Finger Nucleases Made by Oligomerized Pool ENgineering (OPEN)," PLoS One, Feb. 2009, 4(2):e4348.
Foley et al., "Targeted Mutagenesis in Zebrafish Using Customized Zinc Finger Nucleases," Nat. Protoc., 2009, 4(12):1855.
Hess et al., "Zebrafish model for allogeneic hematopoietic cell transplantation not requiring preconditioning," PNAS, Mar. 2013, 110(11):4327-4332.
International Preliminary Report on Patentability in International Application No. PCT/US2014/045963, dated Jan. 12, 2016, 11 pages.
International Search Report and Written Opinion in International Application No. PCT/US2014/045963, dated Nov. 3, 2014, 12 pages.
Iwanami et al., "Genetic Evidence for an Evolutionarily Conserved Role of IL-7 Signaling in T Cell Development of Zebrafish," J. Immunol., 2011, 186:7060-7066.
Joung and Sander, "TALENs: a widely applicable technology for targeted genome editing," Nature Reviews, Jan. 2013, 14:49-55.
Konantz et al., "Zebrafish xenografts as a tool for in vivo studies on human cancer," Ann. NY Acad. Sci., Aug. 2012, 1266:124-137.
Leong et al., "Targeted Mutagenesis of Zebrafish: Use of Zinc Finger Nucleases," Birth Defects Research (Part C), 2011, 93:249-255.
Meng et al., "Targeted gene inactivation in zebrafish using engineered zinc finger nucleases," Nat. Biotechnol., Jul. 2008, 26(6):695-701.
Moore et al., "Improved Somatic Mutagenesis in Zebrafish Using Transcription Activator-Like Effector Nucleases (TALENs)," PLoS One, May 2012, 7:e37877.
Nicoli et al., "Mammalian Tumor Xenografts Induce Neovascularization in Zebrafish Embryos," Cancer Research, 2007, 67:2927-2931.
Reyon et al., "Engineering Designer Transcription Activator—Like Effector Nucleases (TALENs) by REAL or REAL-Fast Assembly," Current Protocols in Molecular Biology, Oct. 2012, Unit 12.15, Supplement 100, 14 pages.

(Continued)

*Primary Examiner* — Valarie E Bertoglio
(74) *Attorney, Agent, or Firm* — Fish & Richardson P.C.

(57) ABSTRACT

Genetically-modified zebrafish lacking one or more immune-related genes, and the use thereof, e.g., in cell or tissue transplantation methods or in stem cell biology. In a first aspect, the invention provides a genetically-modified fish whose genome is homozygous for engineered or induced genetic alteration, e.g., an alteration that changes the sequence of the genomic ONA resulting in insertion and deletion of nucleotides that disrupt protein function or shift the frame of translation leading to premature protein termination, in one or more immune-related genes selected from the group consisting of: foxn1, rag2, jak3, prkdc, and interleukin 2-receptor gamma a and (IL2RGa and IL2RGb), wherein the genetic alteration results in an inactivation (i.e., loss of expression or function) of both alleles of the immune-related gene.

12 Claims, 12 Drawing Sheets
Specification includes a Sequence Listing.

(56) References Cited

OTHER PUBLICATIONS

Sander et al., "Selection-Free Zinc-Finger Nuclease Engineering by Context-Dependent Assembly (CoDA)," Nat. Methods, Jan. 2011, 8:67-69.
Sander et al., "Targeted gene disruption in somatic zebrafish cells using engineered TALENs," Nat. Biotechnol., 29(8):697-698, 2011.
Stoletov et al., "High-resolution imaging of the dynamic tumor cell-vascular interface in transparent zebrafish," PNAS, Oct. 2007, 104(44):17406-17411.
Topczewska et al., "Embryonic and tumorigenic pathways converge via Nodal signaling: role in melanoma aggressiveness," Nature Medicine, Aug. 2006, 12(8):925-932.
Weinholds et al., "Target-Selected Inactivation of the Zebrafish rag1 Gene," Science, Jul. 2002, 297:99-102.
Alexander et al., "Isolation and transcriptome analysis of adult zebrafish cells enriched for skeletal muscle progenitors," Muscle Nerve, May 2011, 43(5): 741-50.
Ali et al., "Zebrafish embryos and larvae: a new generation of disease models and drug screens," Birth Defects Research, 2011, 93(2): 115-33.
Blackburn et al., "Notch signaling expands a pre-malignant pool of T-cell acute lymphoblastic leukemia clones without affecting leukemia-propagating cell frequency," Leukemia, 2012, 26: 2069-2078.
Blackburn et al., "Quantifying the Frequency of Tumor-propagating Cells Using Limiting Dilution Cell Transplantation in Syngeneic Zebrafish," J Vis Exp,, 2011, 53: e2790-e2790.
Blunt et al., "Defective DNA-dependent protein kinase activity is linked to V(D)J recombination and DNA repair defects associated with the murine scid mutation," Cell, Mar. 1995. 80(5): 813-23.
Boehm et al., "Genetic dissection of thymus development in mouse and zebrafish," Immunol Rev, Oct. 2003. 195: 15-27.
Bosma et al., "A severe combined immunodeficiency mutation in the mouse," Nature, 1983, 301(5900): 527-30.
Christianson et al., "Enhanced human CD4+ T cell engraftment in beta2-microglobulin-deficient NOD-scid mice," J Immunol 1997, 158(8): 3578-86.
Cifuentes et al., "A novel miRNA processing pathway independent of Dicer requires Argonaute2 catalytic activity," Science, Jun. 2010, 328(5986): 1694-8.
Corkery et al., "Leukaemia xenotransplantation in zebrafish—chemotherapy response assay in vivo," Br J Haematol, 2011, 153(6): 786-9.
Dahlem et al., "Simple Methods for Generating and Detecting Locus-Specific Mutations Induced with TALENs in the Zebrafish Genome," PLoS Genet, Aug. 2012, 8(8): e1002861.
Ding et al., "DNA-PKcs mutations in dogs and horses: allele frequency and association with neoplasia," Gene, 2002. 283(1-2): 263-9.
Frank et al., "Exposing the human nude phenotype," Nature, 1999, 398(6727): 473-4.
Ghotra et al., "Automated whole animal bio-imaging assay for human cancer dissemination," PLoS One, 2012. 7(2): e31281.
Haldi et al., "Human melanoma cells transplanted into zebrafish proliferate, migrate, produce melanin, form masses and stimulate angiogenesis in zebrafish," Angiogenesis, 2006. 9(3): 139-51.
Hansen and Zapata, "Lymphocyte development in fish and Amphibians," Immunological Reviews, Dec. 1998, 166: 199-220.
Higashijima et al., "High-frequency generation of transgenic zebrafish which reliably express GFP in whole muscles or the whole body by using promoters of zebrafish origin," Dev Biol, 1997, 192(2): 289-99.
Huang et al., "Heritable gene targeting in zebrafish using customized TALENs," Nat Biotechnol, Aug. 2011, 29(8): 699-700.
Ignatius et al., "In Vivo imaging of tumor-propagating cells, regional tumor heterogeneity, and dynamic cell movements in embryonal rhabdomyosarcoma," Cancer Cell 2012. 21(5): 680-93.
Ishikawa et al., "Development of functional human blood and immune systems in NOD/SCID/IL2 receptor {gamma} chain(null) mice," Blood, Sep. 2005, 106(5): 1565-73.

Lamason et al., "SLC24A5, a Putative Cation Exchanger, Affects Pigmentation in Zebrafish and Humans," Science, Dec. 2005, 310(5755):1782-6.
Langenau et al., "Co-injection strategies to modify radiation sensitivity and tumor initiation in transgenic Zebrafish," Oncogene, 2008, 27(30): 4242-8.
Langenau et al., Cre/lox-regulated transgenic zebrafish model with conditional myc-induced T cell acute lymphoblastic leukemia, PNAS, Apr. 2005, 102(17): 6068-73.
Langenau et al., "Effects of RAS on the genesis of embryonal Rhabdomyosarcoma," Genes Dev, 2007, 21(11): 1382-95.
Langenau et al., "In vivo tracking of T cell development, ablation, and engraftment in transgenic zebrafish," PNAS, 2004, 101(19): 7369-74.
Langenau et al., "Myc-induced T cell leukemia in transgenic Zebrafish," Science, 2003, 299(5608): 887-90.
Lee et al., "The fate of human malignant melanoma cells transplanted into zebrafish embryos: assessment of migration and cell division in the absence of tumor formation," Dev Dyn., 2005, 233(4): 1560-70.
Lister et al., "nacre encodes a zebrafish microphthalmia-related protein that regulates neural-crest-derived pigment cell fate," Development, 1999, 126:3757-3767.
Macchi et al., "Mutations of Jak-3 gene in patients with autosomal severe combined immune deficiency (SCID)," Nature, Sep. 1995, 377(6544): 65-8.
Mombaerts et al., "RAG-1-deficient mice have no mature B and T Lymphocytes," Cell, 1992. 68(5): 869-77.
Mosimann et al., "Ubiquitous transgene expression and Cre-based recombination driven by the ubiquitin promoter in zebrafish," Development, 2011, 138(1): 169-77.
Nehls et al., "New member of the winged-helix protein family disrupted in mouse and rat nude mutations," Nature, 1994, 372(6501): 103-7.
Nosaka et al., "Defective lymphoid development in mice lacking Jak3," Science, Nov. 1995, 270(5237): 800-2.
Parichy et al., "An orthologue of the kit-related gene fms is required for development of neural crest-derived xanthophores and a subpopulation of adult melanocytes in the zebrafish, *Danio rerio*," Development, Jul. 2000, 127: 3031-3044.
Parichy et al., "Mutational Analysis of Endothelin Receptor b1 (rose) during Neural Crest and Pigment Pattern Development in the Zebrafish Danio rerio," Dev. Biol., 2000, 227(2):294-306.
Pearson et al., "Non-obese diabetic-recombination activating gene-1 (NOD-Rag1 null) interleukin (IL)-2 receptor common gamma chain (IL2r gamma null) null mice: a radioresistant model for human lymphohaematopoietic engraftment," Clin Exp Immunol, Nov. 2008, 154(2): 270-84.
Perryman, "Molecular pathology of severe combined immunodeficiency in mice, horses, and dogs," Vet Pathol, 2004, 41(2): 95-100.
Pham et al., "Methods for generating and colonizing gnotobiotic zebrafish," Nat Protoc, 2008. 3(12): 1862-75.
Rawls et al., "Reciprocal gut microbiota transplants from zebrafish and mice to germ-free recipients reveal host habitat selection," Cell, Oct. 2006, 127(2): 423-33.
Rawls et al.," Gnotobiotic zebrafish reveal evolutionarily conserved responses to the gut microbiota," PNAS, Mar. 2004, 101(13): 4596-601.
Russell et al., "Mutation of Jak3 in a patient with SCID: essential role of Jak3 in lymphoid development," Science, Nov. 1995, 270(5237): 797-800.
Sander et al., "Engineering zinc finger nucleases for targeted mutagenesis of zebrafish," Methods Cell Biol, 2011, 104: 51-8.
Shultz et al., "Human lymphoid and myeloid cell development in NOD/LtSz-scid IL2R gamma null mice engrafted with mobilized human hemopoietic stem cells," J Immunol,, 2005, 174(10): 6477-89.
Shultz et al., "Multiple defects in innate and adaptive immunologic function in NOD/LtSz-scid mice," J Immunol Jan. 1995, 154(1): 180-91.
Shultz et al., "NOD/LtSz-Rag1null mice: an immunodeficient and radioresistant model for engraftment of human hematolymphoid

(56) References Cited

OTHER PUBLICATIONS cells, HIV infection, and adoptive transfer of NOD mouse diabetogenic T cells," J Immunol, 2000, 164(5): 2496-507.
Shultz et al., "NOD/LtSz-Rag1nullPfpnull mice: a new model system with increased levels of human peripheral leukocyte and hematopoietic stem-cell engraftment," Transplantation, Oct. 2003. 76(7): 1036-42.
Siekmann et al., "Chemokine signaling guides regional patterning of the first embryonic artery," Genes Dev, 2009. 23(19): 2272-7.
Smith et al., "High-throughput cell transplantation establishes that tumor-initiating cells are abundant in zebrafish T-cell acute lymphoblastic leukemia," Blood, Apr. 2010, 115: 3296-3303.
Thomis et al., "Defects in B lymphocyte maturation and T lymphocyte activation in mice lacking Jak3," Science, Nov. 1995, 270(5237): 794-7.
Traver et al., "Effects of lethal irradiation in zebrafish and rescue by hematopoietic cell transplantation," Blood, Sep. 2004, 104(5): 1298-305.
Traver et al., "Transplantation and in vivo imaging of multilineage engraftment in zebrafish bloodless mutants," Nature Immunology, 2003, 4(12):1238-1246.
Trede et al., "The use of zebrafish to understand immunity," Immunity, 2004, 20(4): 367-79.
White et al., "Transparent adult zebrafish as a tool for in vivo transplantation analysis," Cell Stem Cell, Feb. 2008, 2(2): 183-9.
Willett et al., "Early hematopoiesis and developing lymphoid organs in the zebrafish," Developmental Dynamics, 1999, 214(4): 323-36.
Willett et al., "Expression of zebrafish rag genes during early development identifies the thymus," Developmental Biology, 1997. 182(2): p. 331-41.
Zhu et al., "Evaluation and application of modularly assembled zinc-finger nucleases in zebrafish," Development, 2011, 138(20): 4555-64.
Moore et al., "Single-cell imaging of normal and malignant cell engraftment into optically clear prkdc-null SCID zebrafish," J. Exp. Med, 2016, 213: 2575-2589.
Moore et al., "Single-cell transcriptional analysis of normal, aberrant, and malignant hematopoiesis in zebrafish," J. Exp. Med, 2016, 213: 979-992.
Tang et al., "Dissecting hematopoietic and renal cell heterogeneity in adult zebrafish at single-cell resolution using RNA sequencing," J. Exp. Med, 2017, 1-13.
Tang et al., "Imaging tumour cell heterogeneity following cell transplantation into optically clear immune-deficient zebrafish," Nature Communications, 2016, 7:10358.

* cited by examiner

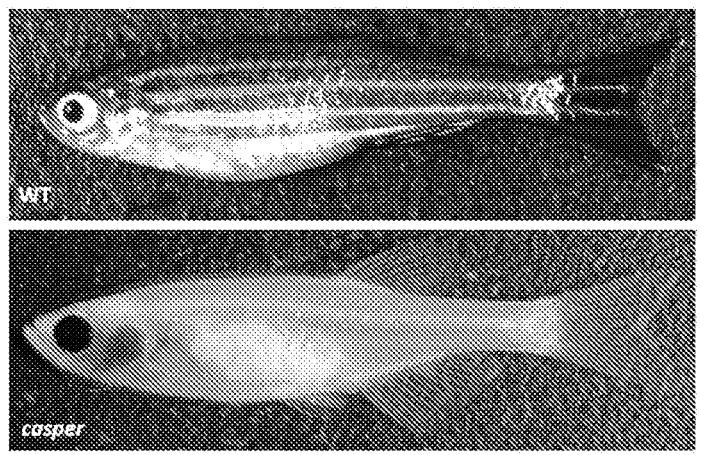
FIG. 1
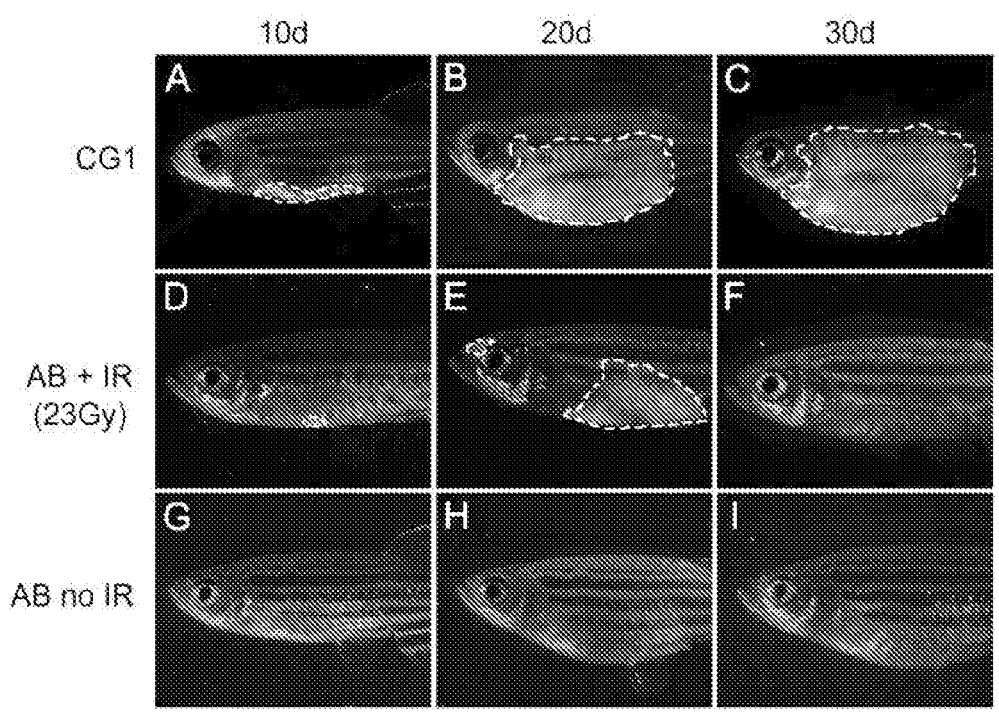
FIGs. 2A-I

```
foxn1, 5 mutant sequences of 34 sequences = 14.7%
TGAAGAGGCAGGTTGTAGGGACGATGTCCTCTGAGCCCCAGGGACTGTCTTTCCTA        WT       [x29]
TGAAGAGGCAGGTTGTAGGGACGATGTCCTCTGAGCCCAGGCAGGGACTGTCTTT         +4       (x1)
TGAAGAGGCAGGTTGTAGGGACGATGTCCTCTGAGCCCAGGGAGACTGTCTTTCC         +2       (x1)
TGAAGAGGCAGGTTGTAGGGACGATGTCCTCTGAGCC                           Δ60      (x1)
TGAAGAGGCAGGTTGTAGGGACGATGTCCTCTGAG          CTGTCTTTCCTA       Δ9       (x1)
TGAAGAGGCAGGTTGTAGGGACGATGTCCTCTGAGCCCATAAGTATCCATAAGTA         Δ14+14   (x1)

dna-pkc, 5 mutant sequences of 67 sequences = 7.5%
TACATGACTGAATTGCTTGGAGATGCCAAGTCTCCAAGATTTGGGTCTTACAGA          WT       [X 62]
TACATGACTGAATTGCTTGGAG--------TCTCCAAGATTTGGGTCTTACAGA          Δ8       (x1)
TACATGACTGAATTGCTTGGAGA-------CTCTCCAAGATTTGGGTCTTACAGA         Δ7+1     (x1)
TACATGACTGAATTGCTTGGAGATG-----TCTCCAAGATTTGGGTCTTACAGA          Δ5       (x2)
TACATGACTGAATTGCTTGGAGA----------GTCCAAGATTTGGGTCTTACAGA        Δ9+1     (x1)

il2rgα, 5 mutant sequences of 83 sequences = 6.0%
TACATTGAAAACAAGCCTGTACCGTGACGATGGCAGTTTGGTGACGGAACAGGA          WT       [X78]
TACATTGAAAACAAGCCTGTAC----------TGGCAGTTTGGTGACGGAACAGGA        Δ8       (x1)
TACATTGAAAACAAGCCTGTACCG--------GCAGTTTGGTGACGGAACAGGA          Δ8       (x1)
TACATTGAAAACAAGCCTGTACCGTG-------GCAGTTTGGTGACGGAACAGGA         Δ6       (x1)
TACATTGAAAACAAGCCTGTACCG------TGGCAGTTTGGTGACGGAACAGGA          Δ6       (x1)
TACATTGAAAACAA-----------AACTGATGGCAGTTTGGTGACGGAACAGGA         Δ10      (x1)

il2rgβ, 10 mutant sequences of 22 sequences = 45.5%
TGTGCAGTGTAAAATCATCAACGTGGACTATGTGGAGTGCATCTGGCAACGGA           WT       [x12]
TGTGCAGTGTAAAATCATCAACGTGGAGTGCATCTG---GCATCTGGCAACGGA          Δ11+9    (x2)
TGTGCAGTGTAAAATCATCAACGTGGT----------GTGCATCTGGCAACGGA          Δ10+1    (x1)
TGTGCAGTGTAAAATCATCAACGTGGA----GTGGAGTGCATCTGGCAACGGA           Δ4       (x1)
TGTGCAGTGTAAAATCATCAAC----------GTGGAGTGCATCTGGCAACGGA          Δ9       (x2)
TGTGCAGTGTAAAATCATCAACGTGGA---------GTGCATCTGGCAATGGA           Δ9       (x1)
TGTGCAGTGTAAAATCATCAACG------TATGTGGAGTGCATCTGGCAACGGA          Δ5       (x1)
TGTGCAGTGTAAAATCATCAACG------ATGTGGAGTGCATCTGGCAACGGA           Δ6       (x1)
TGTGCAGTGTAAAATCATCAACGTGGA---------------------------          Δ26      (x1)
```

FIG. 3

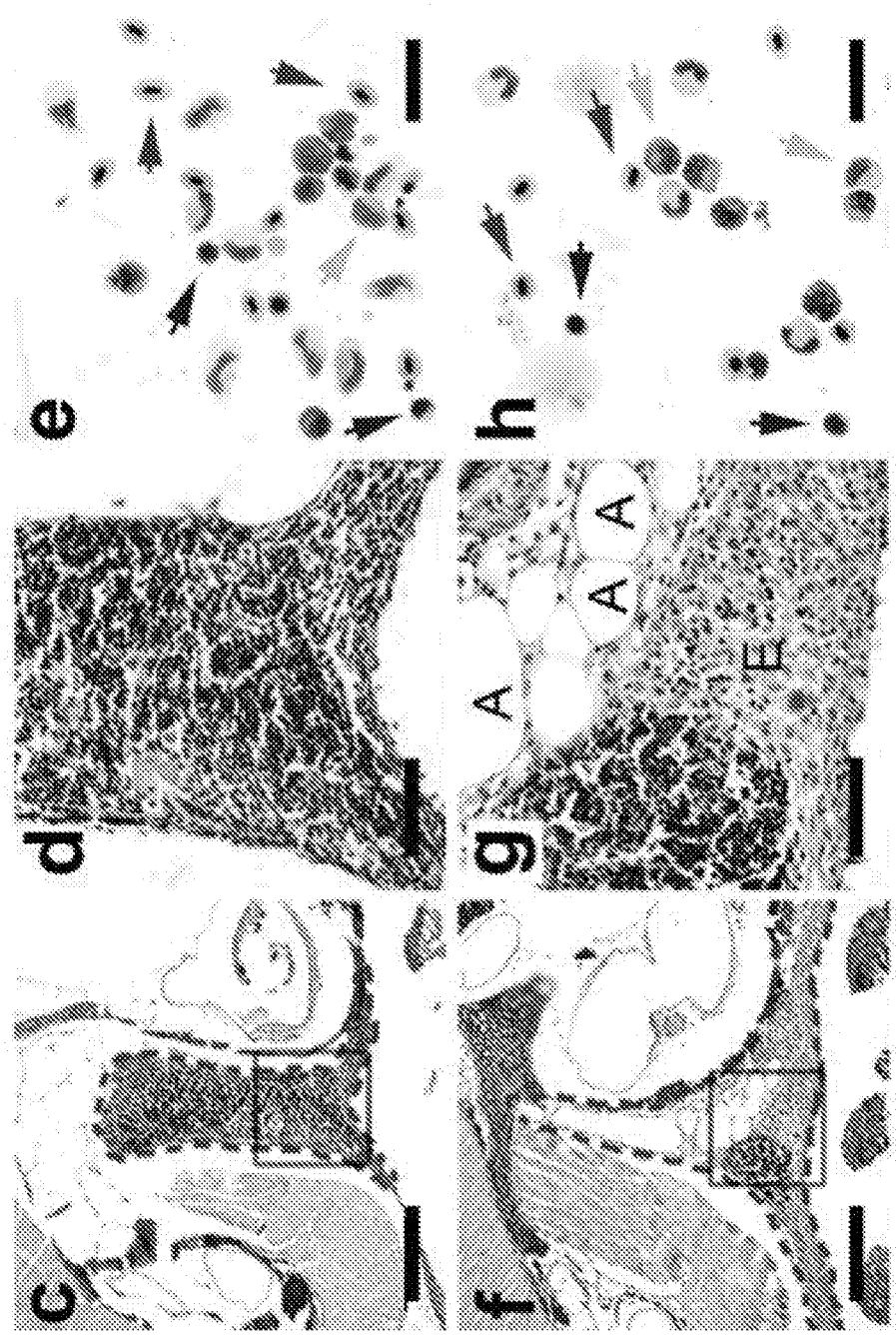
FIG. 4C-H

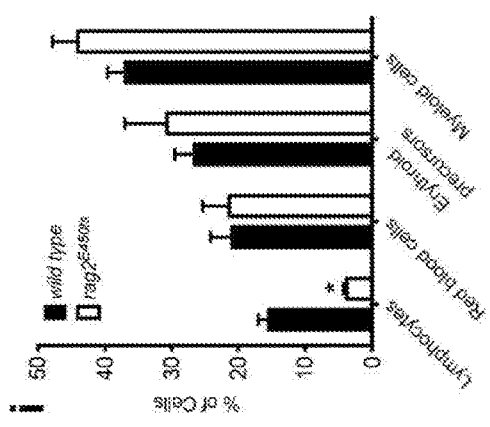
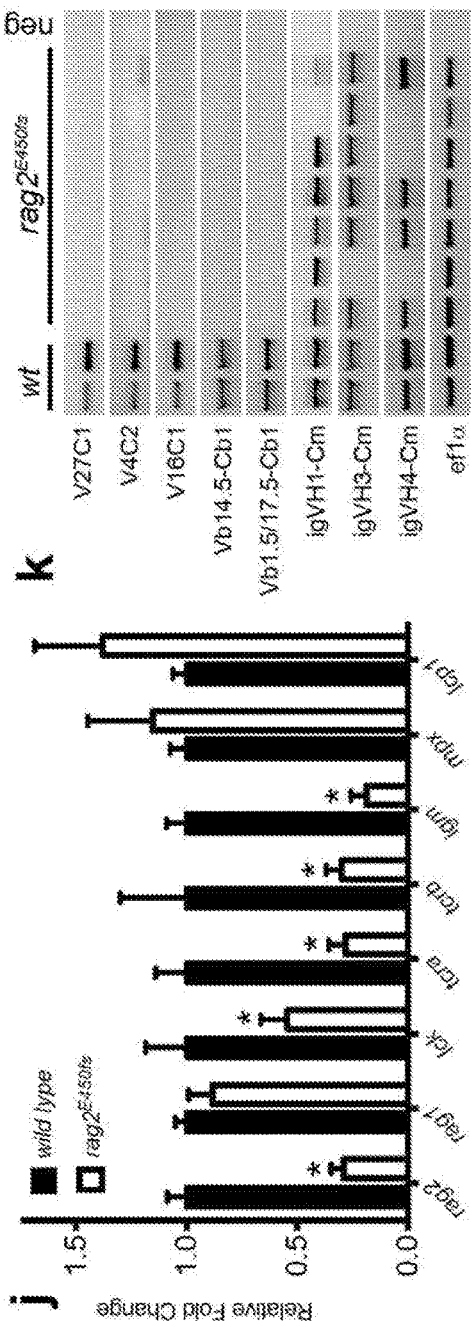
FIG. 4I
FIG. 4J-K

```
rag2-nt    ccatgATCTTCTGCtccaagGTGAAGGTggacactg
Line 6b    ccatgATCTTCTGCtccaaggGGTG        gacactg         (Δ6)
Line 14    ccatgATCTTCTGCTCCAGGGgc AGGTgacactg              (Δ3 and +2)
Line 6a    ccatgATCTTCTGCtccaagGCGggggTGAAGGTggacactg       (+4)
```

```
                                                                          ELTRPAMIFCSRGEGGH
                                                                          ELTRPAMIFCSRGRG GH
                                                                          ELTRPAMIFCSRGQVDT    (Δ450-451)
                                                                          ELTRPAMIFCSRGG..     (449fs-stop)
                                                                                               (449fs-stop)
```

```
jak3-nt    TATTTCTGCGCAGAAGTGgccccaccaagcctgctGGAGGACATACAGAATTA
Line 1     TATTTCTGCGCAGAAGTGgccccca                tGGAGGACATA          (Δ10 and +18)
Line 7,8   TATTTCTGCGCAGAAGTGgcc            tgctGGAGGACATACAGAATTA        (Δ10)
Line 12    TATTTCTGCGCAGAAGTGgccccc                tGGAGGACATACAGAATTA    (Δ11 and +3)
```

```
                                                       YFCAEVAPPSLLEDIQN
                                                       YFCAEVAPTLQDTTWRT    (369fs-stop)
                                                       YFCAEVACVRTSRITAI    (368fs-stop)
                                                       YFCAEVAPAGGHTELLP    (369fs-stop)
```

```
foxn1-nt   TGAAGAGGCAGGTTGTAGggacgATGtccttgagcccCAGGACTGTCTTTCCTA
Line #1    TGAAGAGGCAGGTTGTAGggacgATGtcctctga         GACTGTCTTTCCTA    (Δ9)
Line 11a   TGAAGAGGCAGGTTGTAGggacgATGtcctgagcccCA    GACTGTCTTTCCTA     (Δ2)
```

```
                                                       MSSEPQGLSFLSISSSS
                                                       MSSE---LSFLSISSSS    (Δ5-7)
                                                       MSSEPQTVTFIRK.       (7fs-stop)
```

FIG. 5A

| Gene | Sequence | Lesion |
|---|---|---|
| foxn1 | TCCTCAACCACTGTACCCTAAACCAGTCTACTCCTACAGGTATGTATAGCA | wt |
| | TCCTCAACCACTGTACCCTAAACC--------TCCTACAGGTATGTATAGCA | Δ7 nt |
| | TCCTCAACCACTGTACCCTAAAC---------TCCTACAGGTATGTATAGCA | Δ8 nt |
| | TCCTCAACCACTGTACCCTAAACC----------TACAGGTATGTATAGCA | Δ10 nt |
| | TCCTCAACCACTGTACCCTAAAC----------aaTACAGGTATGTATAGCA | Δ11 +2 nt |
| | TCCTCAACCACTGTACCCTAA-----------CCTACAGGTATGTATAGCA | Δ11 nt |
| | TCCTCAACCACTGTACCCT-------------CCTACAGGTATGTATAGCA | Δ13 nt |
| Il2rga | TACATTGAAAACAAGCCTGTACCGTGACGATGGCAGTTTGGTGACGGAACAGGA | wt |
| | TACATTGAAAACAAGCCTGTACCG---------ATGGCAGTTTGGTGACGGAGTGACA | Δ5 nt |
| | TACATTGAAAACAAGCCTGTACC----------GGCAGTTTGGTGACGGAGTGACA | Δ8 +1 nt |
| | TACATTGAAAACAAGCCTGTACC-----------TGGCAGTTTGGTGACGGAGTGACA | Δ7 nt |
| | TACATTGAAAACAAGCCTGTACATGG-----------TTTGGTGACGGAGTGACA | Δ10 nt |
| | TACATTGAAAACAAGCCTG-----------GCAGTTTGGTGACGGAGTGACA | Δ13 nt |
| | TACATTGAAAACAAGCCTGTACCG-----------CAGTTTGGTGACGGAGTGACA | Δ9 nt |
| Il2rgb | TGTGCAGTGTAAAATCATCAACGTGGACTATGTGGAGTGCATCTGGCAACGGA | wt |
| | TGTGCAGTGTAAAATCATCAACGTGG-----------GTGCATCTGGCAACGGA | Δ10 nt |
| | TGTGCAGTGTAAAATCATCAA-----------TGGAGTGCATCTGGCAACGGA | Δ11 nt |
| | TGTGCAGTGTAAAATCATCAACGTGGAC--------atGAGTGCATCTGGCAACGGA | Δ6 +2 nt |
| | TGTGCAGTGTAAAATCATCAAC-----------ATGTGGAGTGCATCTGGCAACGGA | Δ7 nt |
| | TGTGCAGTGTAAAATCATCAACGTG-----------TGGAGTGCATCTGGCAACGGA | Δ7 nt |
| | TGTGCAGTGTAAAATCATCAACGTGGA-----------GTGCATCTGGCAACGGA | Δ9 nt |

FIG. 5B

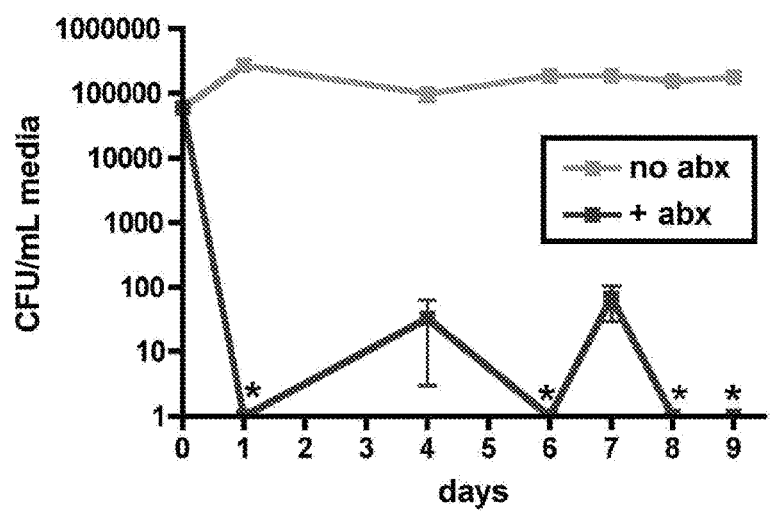

FIG. 6

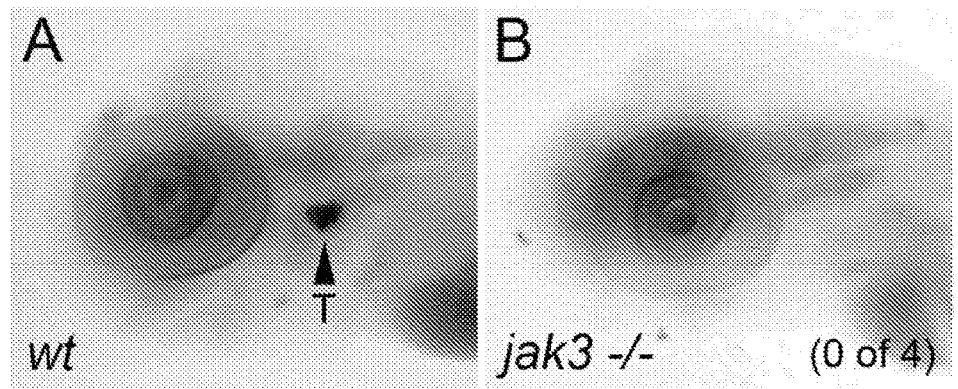
FIGs. 7A-B
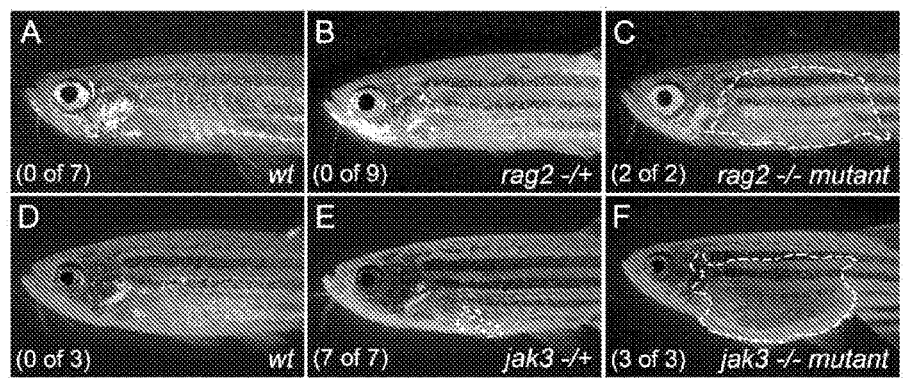
FIGs. 8A-F
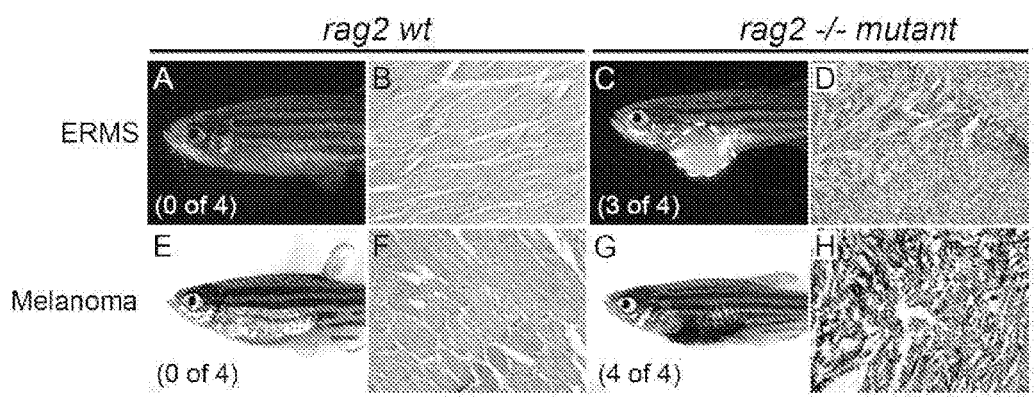
FIGs. 9A-H

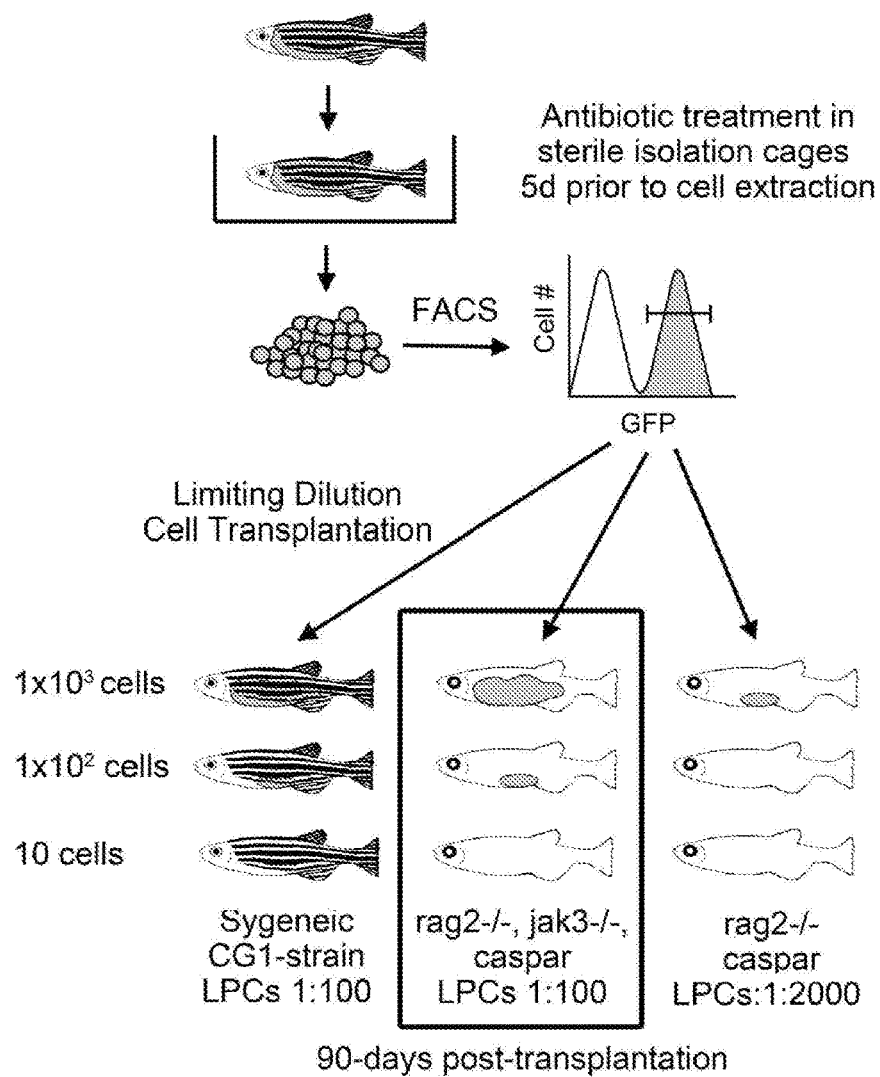
FIG. 10
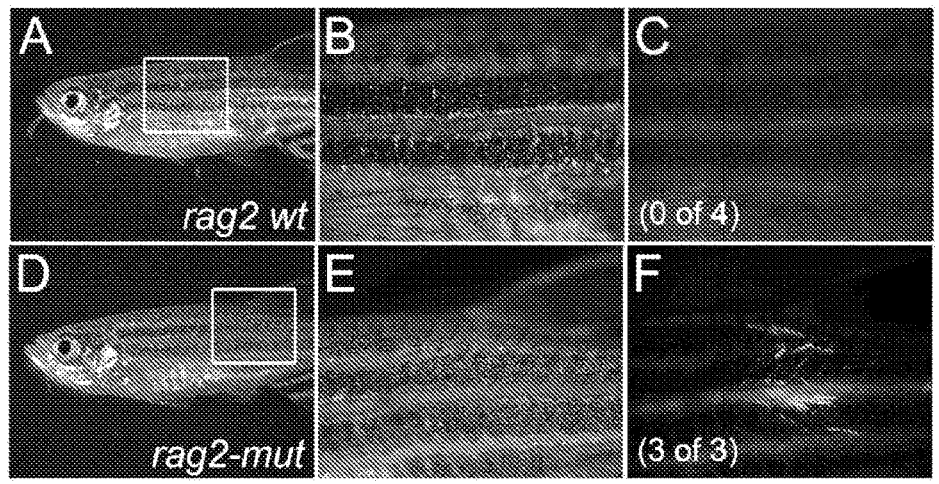
FIGs. 11A-F

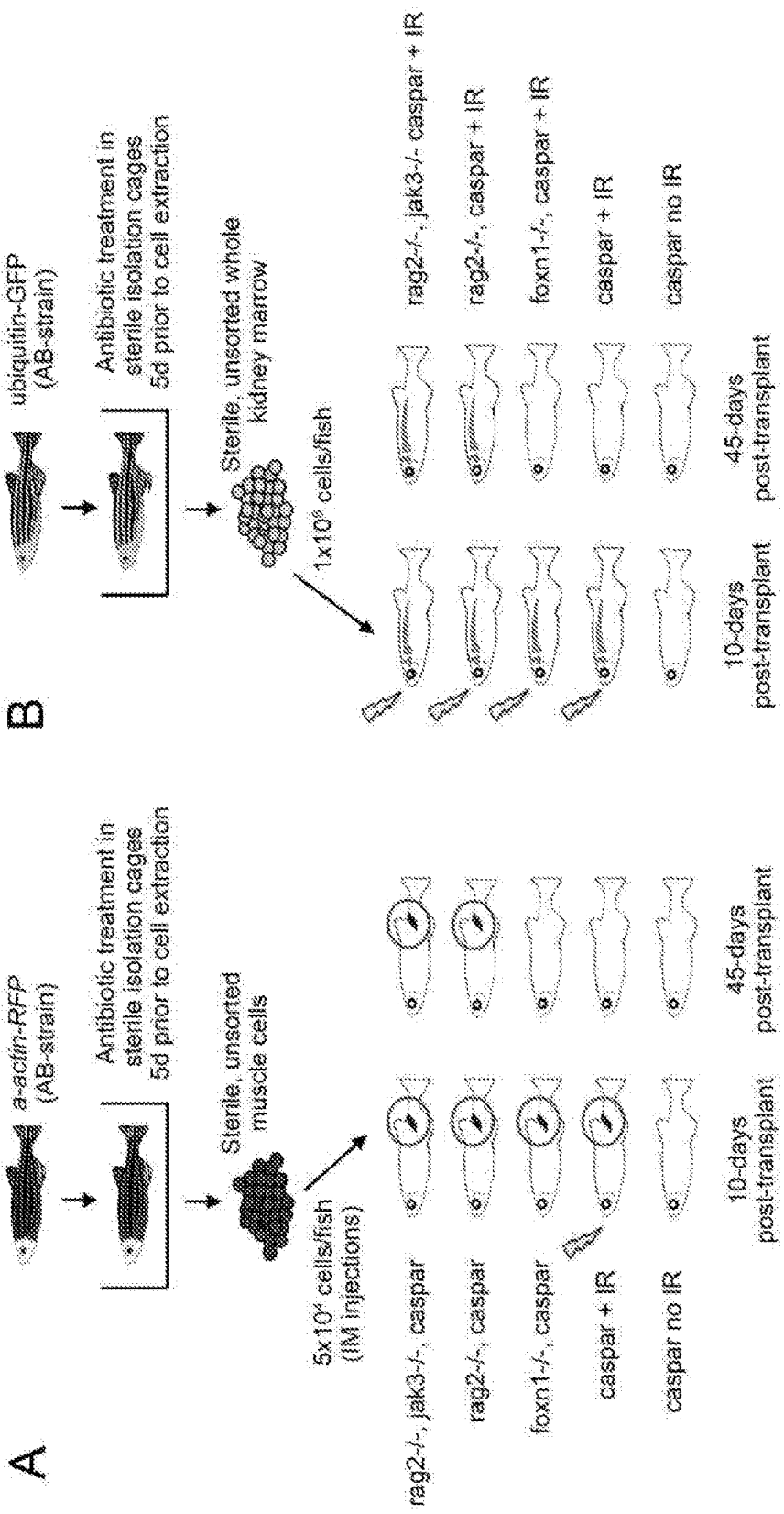
FIGs. 12A-B

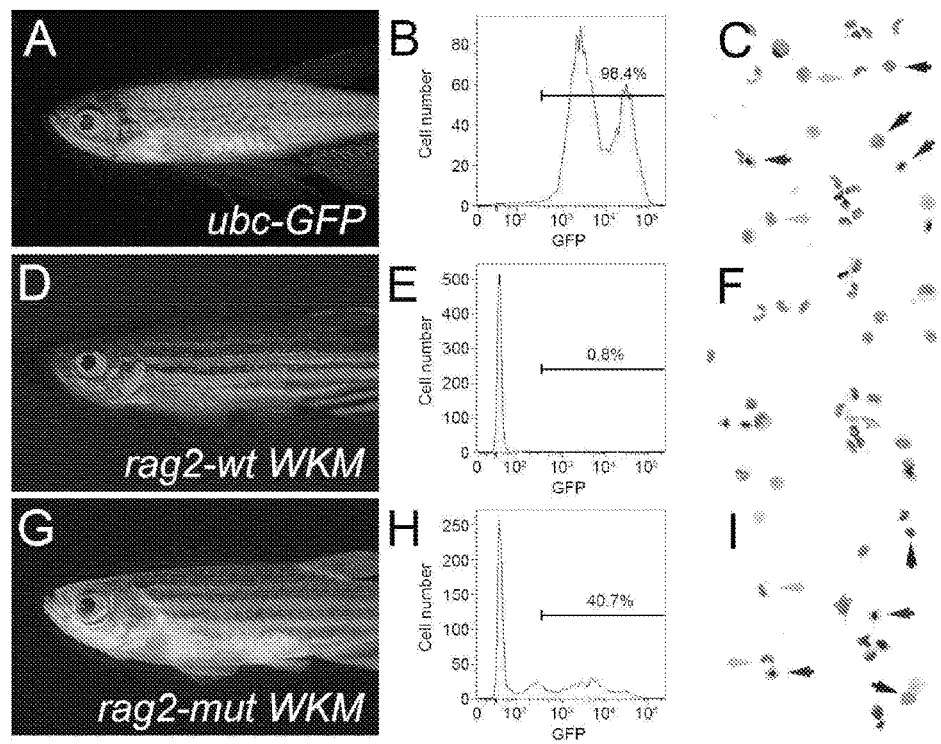
FIGs. 13A-I
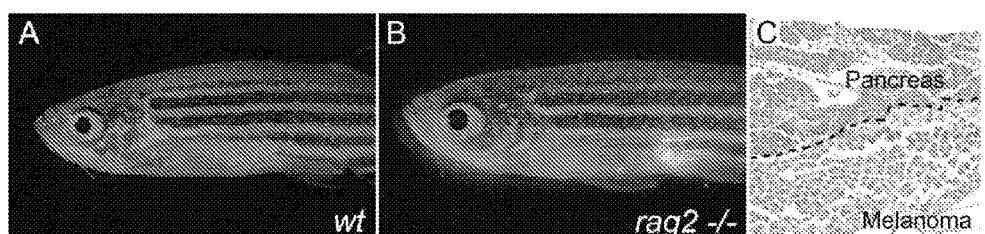
FIGs. 14A-C

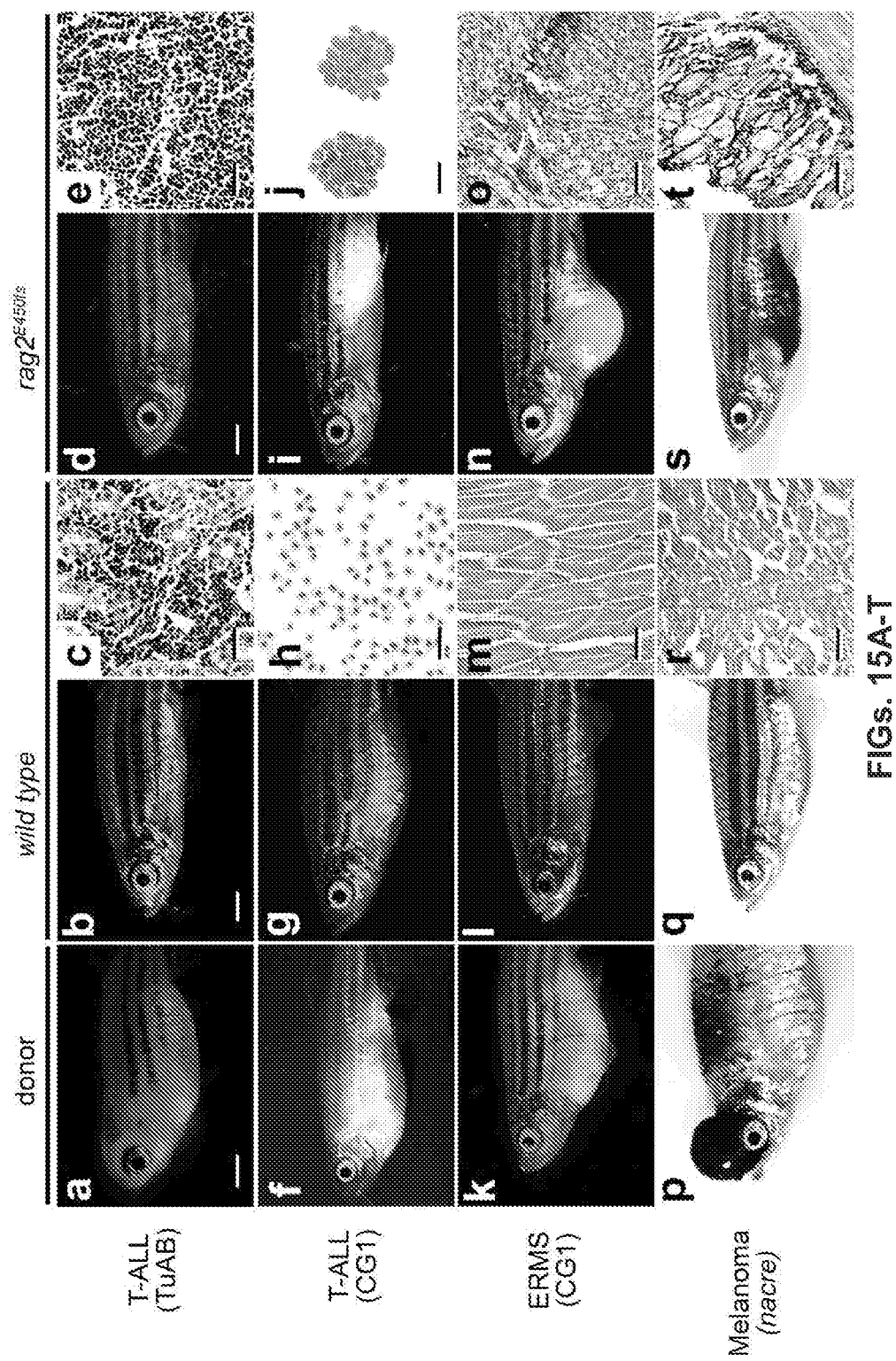
FIGs. 15A-T

SEQUENCE LISTING

```
<160> NUMBER OF SEQ ID NOS: 70

<210> SEQ ID NO 1
<211> LENGTH: 56
<212> TYPE: DNA
<213> ORGANISM: Danio rerio

<400> SEQUENCE: 1
tgaagaggca ggttgtaggg acgatgtcct ctgagcccca gggactgtct ttccta      56
```

<210> SEQ ID NO 2
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tgaagaggca ggttgtaggg acgatgtcct ctgagcccca ggcagggact gtctttt      56

<210> SEQ ID NO 3
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tgaagaggca ggttgtaggg acgatgtcct ctgagcccca gggagactgt ctttcc       56

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tgaagaggca ggttgtaggg acgatgtcct ctgagcc                            37

<210> SEQ ID NO 5
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tgaagaggca ggttgtaggg acgatgtcct ctgagctgtc tttccta                 47

<210> SEQ ID NO 6
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tgaagaggca ggttgtaggg acgatgtcct ctgagcccca taagtatcca taagta       56

<210> SEQ ID NO 7
<211> LENGTH: 54
<212> TYPE: DNA
<213> ORGANISM: Danio rerio

<400> SEQUENCE: 7
tacatgactg aattgcttgg agatgccaag tctccaagat ttgggtctta caga         54

<210> SEQ ID NO 8
<211> LENGTH: 46
<212> TYPE: DNA

-continued

<213> ORGANISM: Artificial Sequence
<220> FEATURE:
<223> OTHER INFORMATION: Description of Artificial Sequence: Synthetic
      oligonucleotide

<400> SEQUENCE: 8
tacatgactg aattgcttgg agtctccaag atttgggtct tacaga                46

<210> SEQ ID NO 9
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tacatgactg aattgcttgg agactctcca agatttgggt cttacaga              48

<210> SEQ ID NO 10
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tacatgactg aattgcttgg agatgtctcc aagatttggg tcttacaga             49

<210> SEQ ID NO 11
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tacatgactg aattgcttgg agagtccaag atttgggtct tacaga                46

<210> SEQ ID NO 12
<211> LENGTH: 54
<212> TYPE: DNA
<213> ORGANISM: Danio rerio

<400> SEQUENCE: 12
tacattgaaa acaagcctgt accgtgacga tggcagtttg gtgacggaac agga       54

<210> SEQ ID NO 13
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tacattgaaa acaagcctgt actggcagtt tggtgacgga acagga                46

<210> SEQ ID NO 14
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 14
tacattgaaa acaagcctgt accggcagtt tggtgacgga acagga        46

<210> SEQ ID NO 15
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tacattgaaa acaagcctgt accgtggcag tttggtgacg gaacagga        48

<210> SEQ ID NO 16
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tacattgaaa acaagcctgt accgtggcag tttggtgacg gaacagga        48

<210> SEQ ID NO 17
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tacattgaaa acaaaactga tggcagtttg gtgacggaac agga        44

<210> SEQ ID NO 18
<211> LENGTH: 53
<212> TYPE: DNA
<213> ORGANISM: Danio rerio

<400> SEQUENCE: 18
tgtgcagtgt aaaatcatca acgtggacta tgtggagtgc atctggcaac gga        53

<210> SEQ ID NO 19
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tgtgcagtgt aaaatcatca acgtggagtg catctggcat ctggcaacgg a        51

<210> SEQ ID NO 20
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tgtgcagtgt aaaatcatca acgtggtgtg catctggcaa cgga        44

<210> SEQ ID NO 21
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tgtgcagtgt aaaatcatca acgtggagtg gagtgcatct ggcaacgga           49

<210> SEQ ID NO 22
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tgtgcagtgt aaaatcatca acgtggagtg catctggcaa cgga                44

<210> SEQ ID NO 23
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tgtgcagtgt aaaatcatca acgtggagtg catctggcaa tgga                44

<210> SEQ ID NO 24
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tgtgcagtgt aaaatcatca acgtatgtgg agtgcatctg gcaacgga            48

<210> SEQ ID NO 25
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tgtgcagtgt aaaatcatca acgatgtgga gtgcatctgg caacgga             47

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tgtgcagtgt aaaatcatca acgtgga                                   27

```
<210> SEQ ID NO 27
<211> LENGTH: 24
<212> TYPE: DNA
<213> ORGANISM: Danio rerio

<400> SEQUENCE: 27
ttctgctcca ggggtgaagg tgga                                           24

<210> SEQ ID NO 28
<211> LENGTH: 23
<212> TYPE: DNA
<213> ORGANISM: Danio rerio

<400> SEQUENCE: 28
ttctgctcca gggggcaggt gga                                            23

<210> SEQ ID NO 29
<211> LENGTH: 18
<212> TYPE: PRT
<213> ORGANISM: Danio rerio

<400> SEQUENCE: 29

Ala Met Ile Phe Cys Ser Arg Gly Glu Gly Gly His Trp Val His Ala
1               5                   10                  15

Gln Cys

<210> SEQ ID NO 30
<211> LENGTH: 18
<212> TYPE: PRT
<213> ORGANISM: Danio rerio

<400> SEQUENCE: 30

Ala Met Ile Phe Cys Ser Arg Gly Gln Val Asp Thr Gly Ser Met Pro
1               5                   10                  15

Asn Ala

<210> SEQ ID NO 31
<211> LENGTH: 37
<212> TYPE: DNA
<213> ORGANISM: Danio rerio

<400> SEQUENCE: 31
ccatgatctt ctgctccagg ggtgaaggtg gacactg                             37

<210> SEQ ID NO 32
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ccatgatctt ctgctccagg ggtggacact g                                   31

<210> SEQ ID NO 33
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
```
ccatgatctt ctgctccagg gggcaggtgg acactg                          36

<210> SEQ ID NO 34
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ccatgatctt ctgctccagg gggggtgaa ggtggacact g                     41

<210> SEQ ID NO 35
<211> LENGTH: 53
<212> TYPE: DNA
<213> ORGANISM: Danio rerio

<400> SEQUENCE: 35
tatttctgcg cagaagtggc cccaccaagc ctgctggagg acatacagaa tta       53

<210> SEQ ID NO 36
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tatttctgcg cagaagtggc cccaactctc caggacacaa catggaggac ata       53

<210> SEQ ID NO 37
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tatttctgcg cagaagtggc ctgctggagg acatacagaa tta                  43

<210> SEQ ID NO 38
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tatttctgcg cagaagtggc ccctgctgga ggacatacag aatta                45

<210> SEQ ID NO 39
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tgaagaggca ggttgtaggg acgatgtcct ctgaactgtc tttccta              47

```
<210> SEQ ID NO 40
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tgaagaggca ggttgtaggg acgatgtcct ctgagcccca gactgtcttt ccta          54

<210> SEQ ID NO 41
<211> LENGTH: 17
<212> TYPE: PRT
<213> ORGANISM: Danio rerio

<400> SEQUENCE: 41

Glu Leu Thr Arg Pro Ala Met Ile Phe Cys Ser Arg Gly Glu Gly Gly
 1               5                  10                  15

His

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Glu Leu Thr Arg Pro Ala Met Ile Phe Cys Ser Arg Gly Gly His
 1               5                  10                  15

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Glu Leu Thr Arg Pro Ala Met Ile Phe Cys Ser Arg Gly Gln Val Asp
 1               5                  10                  15

Thr

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Glu Leu Thr Arg Pro Ala Met Ile Phe Cys Ser Arg Gly Gly
 1               5                  10

<210> SEQ ID NO 45
<211> LENGTH: 17
<212> TYPE: PRT
<213> ORGANISM: Danio rerio

<400> SEQUENCE: 45

Tyr Phe Cys Ala Glu Val Ala Pro Pro Ser Leu Leu Glu Asp Ile Gln
 1               5                  10                  15
```

Asn

```
<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46
```

Tyr Phe Cys Ala Glu Val Ala Pro Thr Leu Gln Asp Thr Thr Trp Arg
1               5                   10                  15

Thr

```
<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47
```

Tyr Phe Cys Ala Glu Val Ala Cys Trp Arg Thr Ser Arg Ile Thr Ala
1               5                   10                  15

Thr

```
<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48
```

Tyr Phe Cys Ala Glu Val Ala Pro Ala Gly Gly His Thr Glu Leu Leu
1               5                   10                  15

Pro

```
<210> SEQ ID NO 49
<211> LENGTH: 17
<212> TYPE: PRT
<213> ORGANISM: Danio rerio

<400> SEQUENCE: 49
```

Met Ser Ser Glu Pro Gln Gly Leu Ser Phe Leu Ser Ile Ser Ser Ser
1               5                   10                  15

Ser

```
<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50
```

Met Ser Ser Glu Leu Ser Phe Leu Ser Ile Ser Ser Ser Ser
1               5                   10

-continued

```
<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Met Ser Ser Glu Pro Gln Thr Val Phe Pro Ile His Lys
1               5                   10

<210> SEQ ID NO 52
<211> LENGTH: 51
<212> TYPE: DNA
<213> ORGANISM: Danio rerio

<400> SEQUENCE: 52
tcctcaacca ctgtacccta aaccagtcta ctcctacagg tatgtatagc a          51

<210> SEQ ID NO 53
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tcctcaacca ctgtacccta aacctcctac aggtatgtat agca                  44

<210> SEQ ID NO 54
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
tcctcaacca ctgtacccta aactcctaca ggtatgtata gca                   43

<210> SEQ ID NO 55
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
tcctcaacca ctgtacccta aacctacagg tatgtatagc a                     41

<210> SEQ ID NO 56
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tcctcaacca ctgtacccta aacaatacag gtatgtatag ca                    42

<210> SEQ ID NO 57
<211> LENGTH: 40
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 57
tcctcaacca ctgtacccta acctacaggt atgtatagca                              40

<210> SEQ ID NO 58
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
tcctcaacca ctgtaccctc ctacaggtat gtatagca                                38

<210> SEQ ID NO 59
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
tacattgaaa acaagcctgt accgatggca gtttggtgac ggagtgaca                    49

<210> SEQ ID NO 60
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
tacattgaaa acaagcctgt accaggcagt ttggtgacgg agtgaca                      47

<210> SEQ ID NO 61
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tacattgaaa acaagcctgt acctggcagt ttggtgacgg agtgaca                      47

<210> SEQ ID NO 62
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
tacattgaaa acaagcctgt acatggtttg gtgacggagt gaca                         44

<210> SEQ ID NO 63
<211> LENGTH: 41
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 63
tacattgaaa acaagcctgg cagtttggtg acggagtgac a                              41

<210> SEQ ID NO 64
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
tacattgaaa acaagcctgt accgcagttt ggtgacggag tgaca                          45

<210> SEQ ID NO 65
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
tgtgcagtgt aaaatcatca acgtgggtgc atctggcaac gga                            43

<210> SEQ ID NO 66
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tgtgcagtgt aaaatcatca atggagtgca tctggcaacg ga                             42

<210> SEQ ID NO 67
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
tgtgcagtgt aaaatcatca acgtggacat gagtgcatct ggcaacgga                      49

<210> SEQ ID NO 68
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
tgtgcagtgt aaaatcatca acatgtggag tgcatctggc aacgga                         46

<210> SEQ ID NO 69
<211> LENGTH: 46
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 69
tgtgcagtgt aaaatcatca acgtgtggag tgcatctggc aacgga                    46

<210> SEQ ID NO 70
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
tgtgcagtgt aaaatcatca acgtggagtg catctggcaa cgga                      44
```

IMMUNE-COMPROMISED ZEBRAFISH

CLAIM OF PRIORITY

This application is a U.S. National Phase Application under 35 U.S.C. § 371 of International Patent Application No. PCT/US2014/045963, filed on Jul. 9, 2014, which claims the benefit of U.S. Provisional Patent Application Ser. No. 61/844,694, filed on Jul. 10, 2013. The entire contents of the foregoing are hereby incorporated by reference.

FEDERAL FUNDING

This invention was made with government support under Grant. No. R24OD016761 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Aug. 29, 2017, is named 00786-0893US1 SL.txt and is 16,215 bytes in size.

TECHNICAL FIELD

This invention relates to genetically-modified zebrafish lacking one or more immune-related genes, and the use thereof, e.g., in cell or tissue transplantation methods or in stem cell biology.

BACKGROUND

Cell transplantation of human and mouse cells into immune compromised mice has greatly impacted our understanding of stem cell function, regeneration following injury, and cancer. However, these transplantation experiments routinely utilize small cohorts of mice due to high husbandry costs and engraftment of cells is difficult to visualize especially at single cell resolution.

SUMMARY

Capitalizing on the transparent nature of zebrafish, described herein are mutant zebrafish lines that have impaired immune cell function resulting from genetic mutations in one or more immune-related genes.

In a first aspect, the invention provides a genetically-modified fish whose genome is homozygous for an engineered or induced genetic alteration, e.g., an alteration that changes the sequence of the genomic DNA resulting in insertion and deletion of nucleotides that disrupt protein function or shift the frame of translation leading to premature protein termination, in one or more immune-related genes selected from the group consisting of: foxn1 (e.g., as shown in FIG. 3 or 5), rag2 (e.g., as shown in FIG. 5), jak3 (e.g. as shown in FIG. 5A), prkdc (e.g., as shown in FIG. 3), and interleukin 2-receptor gamma a and b (IL2RGa and IL2RGb), (e.g., as shown in FIG. 3); wherein the genetic alteration results in an inactivation (i.e., loss of expression or function) of both alleles of the immune-related gene.

In another aspect, the invention provides a genetically-modified fish whose genome is homozygous for an engineered or induced genetic alteration in both alleles of rag2, wherein the genetic alteration is hypomorphic, i.e., results in a partial inactivation of rag2 (e.g., as shown in FIG. 5).

In some embodiments, the genome of the fish further comprises inactivating genetic alterations in both alleles of jak3 (e.g., as shown in FIG. 5).

In some embodiments, the genome of the fish comprises inactivating genetic alterations in both alleles of: 1) rag2 and jak3; 2) rag2, Il2rga and Il2rgb; 3) prkdc and jak3; or 4) prkdc, Il2rga and Il2rgb.

In an additional aspect, the invention provides methods for growing a mammalian cell, the method comprising transplanting the mammalian cells into a genetically-modified fish as described herein. In some embodiments, the cells are tumor cells, stem cells or progeny of differentiated stem cells.

In another aspect, the invention provides methods for identifying a candidate therapeutic compound for the treatment of a mammalian tumor. The methods include transplanting cells from a mammalian tumor into a genetically-modified fish as described herein; contacting the fish with a test compound; evaluating the growth of the mammalian tumor cells in the presence of the test compound; comparing the level of growth of the mammalian tumor cells in the presence of the test compound to a reference level; and identifying a compound that decreases the level growth of the mammalian tumor cells as a candidate therapeutic compound.

In some embodiments, the mammalian tumor cells are from a subject with cancer, and the method further comprises administering the identified candidate therapeutic compound to the subject.

In yet another aspect, the invention provides methods for detecting an effect of a test compound on development of a cell or tissue. The methods include transplanting a stem or progenitor cell into a genetically-modified fish as described herein; contacting the fish with a test compound for a time sufficient for the stem or progenitor cell to develop; evaluating the development of the stem or progenitor cell or its progeny in the presence of the test compound; comparing the development of the stem or progenitor cell or its progeny in the presence of the test compound to development of the stem or progenitor cell or its progeny in the absence of the test compound; and identifying an effect of the test compound on development of the stem or progenitor cell or its progeny.

In some embodiments, the stem or progenitor cell is labeled, e.g., expresses a fluorescent protein or other detectable marker.

In some embodiments, identifying an effect of the test compound on development of the stem or progenitor cell or its progeny comprises visualization of the cells in vivo or sectioning and staining the cells.

In some embodiments, the test compound is a drug or genetic modification.

In some embodiments, a genetically modified fish has a mutation or mutations selected from 1) foxn1−/−, 2) rag2−/−, 3) jak3−/− single mutant fish, and compound mutants for 4) rag2−/−, jak3−/−; 5) rag2−/−, Il2rga−/−, Il2rgb−/−; 6) prkdc−/−, jak3−/−; and 7) prkdc−/−, Il2rga−/−, Il2rgb−/−. The symbol "−/−" indicates that there is an inactivating mutations in both alleles of the indicated gene, i.e., that the fish is homozygous.

Herein, genetically-modified fish is a fish having an engineered or induced genetic alteration in its genome. Such genetic modifications include those induced using a ZFN or TALEN as described herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1. Optically clear adult zebrafish strains lack pigment. Adult Casper fish result from the cross between nacre and roy mutant fish (bottom). Animals must be maintained in a double homozygous mutant background. Wild-type AB strain (top).

FIGS. 2A-I. Immune barriers prevent long-term engraftment of zebrafish cells into non-immune matched animals. GFP+ T-cell leukemias from CG1-strain, syngeneic zebrafish engraft robustly into non-irradiated CG1 recipients ($1 \times 10^3$ cells/animal, A-C) but are rejected in non-immune matched AB-strain, irradiated animals due to immune system recovery by 30d post-transplant (D-F). T-ALL fail to engraft into non-immune matched animals without irradiating prior to transplant (G-H). Tumor outlined by dotted lines.

FIG. 3. Newly created TALENs induce mutations within target DNA sequences of mosaic injected zebrafish for all genes outlined in this application. Figure discloses SEQ ID NOs:1-26, respectively, in order of appearance.

FIGS. 4A-K. TALENs and ZFNs mutate endogenous zebrafish genes. (a) Zebrafish proteins and domain structures with associated SCID mutations denoted by dots and text bellow proteins. Human SCID mutations are unlabeled; mouse denoted by "m", rat by "r", and dog by "d". Complementary zebrafish amino acids are shown in parenthesis. ZFNs that induce mutations are denoted above proteins as open triangles. TALENS that induce mutations are denoted as filled triangles. (b) Nucleotide (top) and protein (bottom) sequence for rag2E450fs hypomorphic allele (also designated herein as "rag2 line 14"). Highlighted text in the top line denotes the ZFN arms, and highlighted text denotes nucleotide additions and highlighted dashes represent nucleotide deletions. Figure discloses SEQ ID NOS 27-30, respectively, in order of appearance. (c-i) Morphological assessment of lymphocytes in the thymus and marrow. Hematoxylin and eosin stained sections of the thymus from 90-day-old wild type (c-d) and rag2E450fs homozygous mutant zebrafish (f-g). Thymus is outlined by a dotted line (c,f). Amplified views of boxed regions (d,g) with adipocytes (A) and vacant thymic epithelium (E) noted. (e,h) Cytospins of whole kidney marrow with lymphocytes (dark grey arrows), erythrocytes (medium grey arrows) and granulocytes (light grey arrows) denoted. (i) Quantification of hematopoietic cell populations. (j) Gene expression analysis of whole kidney marrow cells. (k) tcrb and igm rearrangement in whole kidney marrow cells. Negative control, neg. Scale bars, 200 mm in c,f; 50 mm in d,g; 20 mm in e,h.

FIGS. 5A-B. Identification of mutant lines. The wild-type nucleotide (nt) sequence is shown at the top left with ZFN and TALEN half-sites highlighted. Deletions are indicated by grey highlighted dashes, and insertions by highlighted nucleotides. The net number of nucleotides inserted or deleted is shown. Amino acid number and sequence for each mutant are shown to the right. Mutations that lead to early frame-shift termination noted (fs-stop). 5A, rag2, jak3, and foxn1 (nucleotide sequences disclosed as SEQ ID NOS 31-38, 1, and 39-40, and amino acid sequences disclosed as SEQ ID NOS 41-51, all respectively, in order of appearance); 5B, foxn1, il2rga and Il2rgb identified founder alleles (SEQ ID NOS 52-58, 12, 59-64, 18, and 65-70, respectively, in order of appearance). Bold indicates TALEN binding sites in 5B. Wild-type/normal DNA sequence (wt). Deletions (Δ).

FIG. 6. Antibiotic treatment reduces microbiota in adult zebrafish. Microbial CFU analysis of media in vessels housing adult zebrafish treated or untreated with an antibiotic cocktail for 9 days. Asterisks indicate CFU levels below detectable limits.

FIGS. 7A-B. Homozygous jak3-deficient zebrafish (line 7.8) lack rag1+ T cells in the thymus at 5 day of life as assessed by whole mount RNA in situ hybridization (n=5 of 5). (A) Wild-type sibling (T, thymus), (B) Mutant fish (all 4 fish were negative for T cells at 5 days post-fertilization (dpf)).

FIGS. 8A-F. rag2- and jak3-deficient zebrafish permit engraftment of unmatched T-ALL cells. Merged fluorescence images at 35d (A-C) or 10d post-transplant (D-F, $1 \times 10^5$ cells/fish). Tumor outlined by dotted lines. Engrafted fish compared to total fish transplanted is noted in parenthesis.

FIGS. 9A-H. Zebrafish fluorescent-labeled rhabdomyosarcoma (ERMS, $5 \times 10^4$ cells/fish) and BRAFV600E-expressing melanoma ($5 \times 10^5$ cells/fish) can robustly engraft into rag2-mutant fish, but not wild-type siblings. Merged fluorescence images of whole fish at 45d post-transplant (A,C,E,G). Tumor outlined by dotted lines (C,G). Number of engrafted fish compared to total shown in parenthesis. Histology of wild-type sibling (B,F) or engrafted mutant fish (D,H, 400×).

FIG. 10. Limiting dilution cell transplantation of fluorescently-labeled T-ALL cells to quantitatively assess each model for engraftment potential. For example, when GFP+ leukemic cells from CG1-strain fish engraft into syngeneic recipients, LPC frequency is 1 in 100. Models that exhibit similar LPC frequency are completely immune compromised (in this example, rag2–/–, jak3–/– fish engraft T-ALL with 1 in 100 cells).

FIGS. 11A-F. rag2-deficient zebrafish engraft unmatched muscle cells from ubiquitin-GFP+ transgenic zebrafish. GFP+ fibers are easily discernable in rag2 mutant fish at high power (F). Non-engrafted wild-type sibling (wt, A-C) and homozygous rag2 mutant fish (D-F) at 45d post-transplant.

FIGS. 12A-B. Schematic for identifying mutant lines that engraft muscle and hematopoietic stem cells.

Figures 4A, 4B:
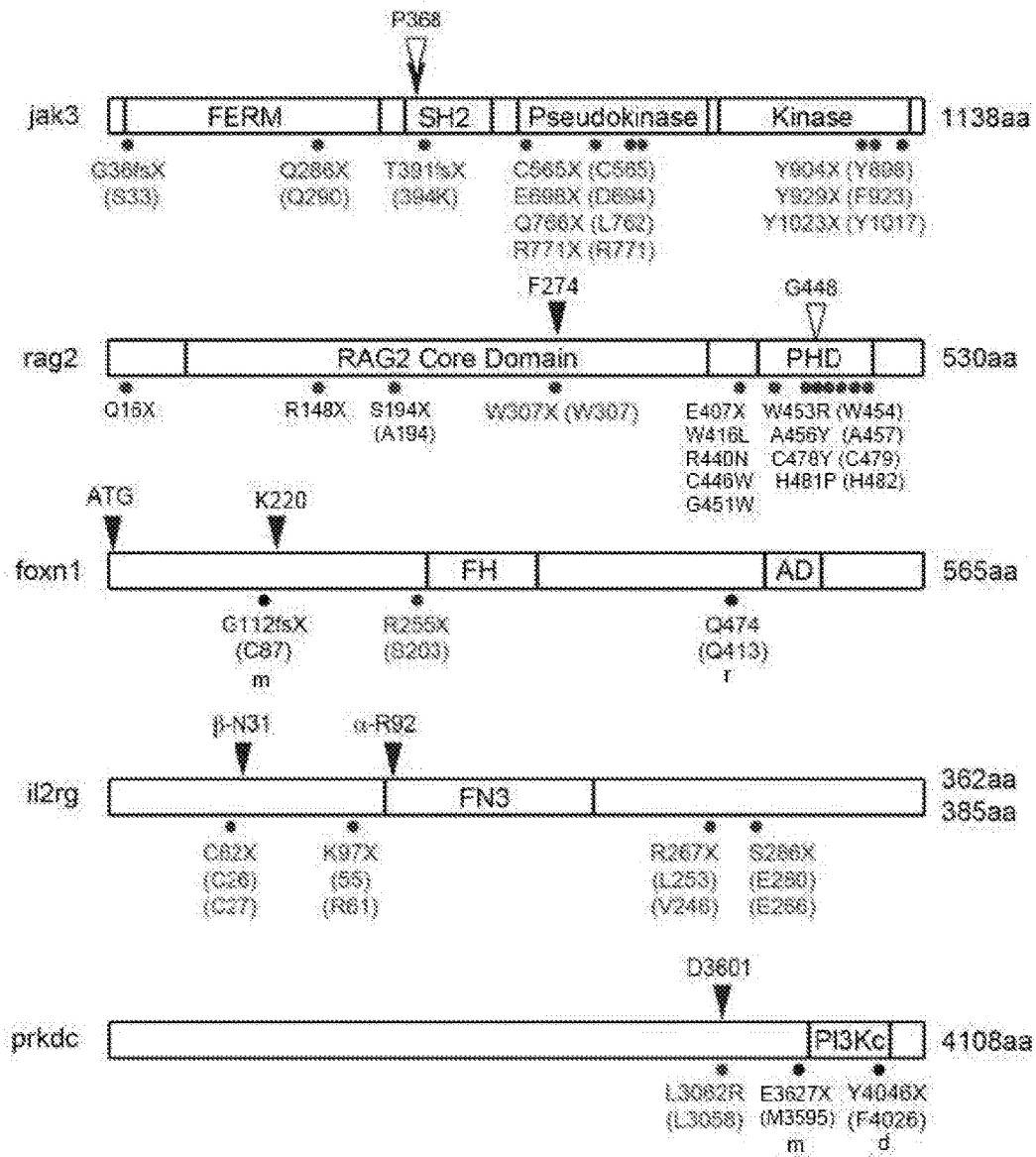

(A) Engraftment of alpha-actin-RFP+ zebrafish muscle stem and progenitor cells. Red circles denote engraftment.

(B) Engraftment of ubiquitin-GFP+ blood stem cells into sub-lethally irradiated recipient fish. Irradiation is required for clearing the HSC niche for colonization by engrafted cells.

FIGS. 13A-I. rag2-homozygous mutant zebrafish permit robust multi-lineage engraftment of HSCs from kidney marrow cells at 45 days post-transplant. Ubiquitin-GFP (ubc-GFP) transgenic line (A-C), wild-type sibling (D-F) and rag2 homozygous mutant fish engrafted with $1 \times 10^6$ cells following 10 Gy irradiation. Whole animal imaging (A,D, G). FACS of kidney (B,E,H). Cytospins of GFP sorted cells (C,I) or unsorted marrow from wild-type non-engrafted fish (F). Lymphoid (dark grey arrows), myeloid (light grey arrows) and red blood cells (medium grey arrows).

FIGS. 14A-C. rag2-deficient zebrafish engraft GFP-labeled human MM383 melanoma cells (n=4 of 9 animals, 1×10$^5$ cells/fish). (A-B) Bright field images of transplant animals at 7d days post-injection. (C) Histology of amelanotic human melanoma growing adjacent the pancreas. Note the large size of human cells compared with fish.

FIGS. 15A-T. Successful engraftment of zebrafish tumors into homozygous rag2$^{E450fs}$ mutant fish. (a-e) dsRED-labeled Myc-induced T-ALL arising in TuAB strain fish, (f-j) zsYellow-labeled T-ALL arising in syngeneic CG1-strain fish, (k-o) GFP-labeled kRASG12D-induced embryonal rhabdomyosarcoma (ERMS) arising in CG1-strain fish, and (p-t) melanomas arising in p53-deficient nacre strain fish injected with transgenes that overexpress mitfa and BRAFV600E. Donor tumors (a,f,k,p). Merged bright-field and fluorescent images of wild type recipient fish at 30 days post-transplantation (b,g,l,q) and subsequent histological analysis of whole kidney marrow (c) or cytospins of peripheral blood (h), and skeletal muscle (m,r). Arrows in c denote large numbers of red blood cells and renal tubules (RT) which are replaced by lymphoid blasts in homozygous rag2$^{E450fs}$ mutant fish engrafted with T-ALL. Engrafted rag2$^{E450fs}$ mutant animals at 30 days post-transplantation (d,i,n,s) and histological analysis of marrow (e) or cytospins of blasts (j). Histology of ERMS (o) and melanoma infiltrating the muscle (t). Scale bars 2 mm in a,b,d,f,g,i,k,l,n,p, q,s, 50 mm in m,o,r,t, 25 mm in c,e, and 20 mm, h and j.

DETAILED DESCRIPTION

Immune compromised mice have been transformative in assessing the cellular functions of normal stem cell fractions and malignant cells in both mouse and human. For example, cell transplantation into immune compromised mice has been used extensively to identify stem and progenitor cells in various tissues including muscle [1-5], blood [6-12], skin [13], heart [14], and endodermal tissues including pancreatic beta-cells [15], hepatocytes, and, intestine [16, 17] and to assess regenerative capacity in a wide range of normal, aged, and diseased tissues. Cell engraftment into immune compromised mice is also a powerful experimental platform to uncover mechanistic insights into self-renewal, homing, migration, and regeneration in vivo.

To date, xenograft transplantation has utilized adoptive transfer of human cells into immune compromised mice including Nude (Foxn1-deficient) [18], NOD/SCID (NOD strain mice with DNA-dependent protein kinase, catalytic subunit-deficiency (Prkdc)) [19-21], and Rag-deficient strain animals [22, 23]. These strains lack fully functional T and/or B cells, but retain largely intact natural killer (NK)-cell function. For example, Non Obese Diabetic strain mice—commonly known as NOD mice—lack complement activity, have defects in myeloid development and antigen presentation, and have reduced NK cell activity. Nude mice have impaired thymic epithelial development resulting in disrupted T-lymphopoiesis. By contrast, Rag2- and Prkdc-deficient mice are unable to recombine T- and B-cell receptors, resulting in loss of functional lymphocytes. To obviate innate immune rejection mediated by NK cells, investigators have utilized Interleukin-2-gamma receptor (Il2rg)-deficient mice [24-26]. Il2rg heterodimerizes with a wide array of cytokine-specific interleukin receptors to orchestrate the cell signaling required for T and NK cell maturation. Creation of NOD/SCID/Il2rg−/− mice has resulted in nearly complete immune compromised animals and have facilitated robust adoptive transfer of both mouse and human cells into recipient animals [25, 26]. NK cell function can also be disrupted by inactivation of B2-microglobulin (B2m), perforin (Prf1), and janus kinase 3 (Jak3) [27] [27-30]. In total, a large number of immune compromised mouse models have been developed for use in cell transfer experiments.

Evolutionarily conserved pathways regulate immune competency. In fact, morpholino and gene inactivation studies in zebrafish has shown that jak3, rag1/2, and foxn1 regulate lymphocyte cell development [31-33], yet SCID phenotypes in adult fish and use of mutant zebrafish as recipients in cell transplantation have yet to be described. Creation of zebrafish deficient for jak3, foxn1, rag2, prkdc, and Il2rg will likely provide powerful models for cell transplantation of zebrafish, mouse, and human cells—facilitating the next generation of low-cost, high throughput cell transplantation models.

Zebrafish have many attributes that represent clear advantages over more commonly used vertebrate models, including 1) fecundity: each female can produce 100-200 eggs per week; 2) small size: thousands of animals can be reared in a relatively small space; 3) reduced cost: mouse per diems range from $0.20-$1.00/day depending on cage size, while fish per diems are <$0.01/day, 4) optical clarity: engraftment of normal and malignant cells can be easily visualized by fluorescent labeling and direct visualization of engrafted cells can be further enhanced by zebrafish lines that lack pigment—aptly called Casper (FIG. 1) [34]; 5) wide temperature range: zebrafish can be reared at 18° C.-35° C., the latter mimicking temperatures seen in mouse and human, 6) high-throughput cell transplantation: 350+ adult syngeneic zebrafish can be transplanted intraperitoneally or retro-orbitally with fluorescently-labeled cancer cells by one investigator in a single day, facilitating large scale experimentation (FIG. 2) [35-39]. To date, the major hurdle for use of zebrafish as a xenograft transplant model is lack of immune-compromised zebrafish strains.

Blood development and function are highly conserved between zebrafish, mouse, and human [40-44]. Zebrafish have a well-developed acquired and innate immune system that develops during the first weeks of life that can detect and kill foreign cells. Zebrafish have T, B, and NK cells as well as myeloid, erythroid, and precursor cell populations. Capitalizing on the short window of immune tolerance in early larval development, investigators have utilized cell transplantation of human cancer cells into 2-day-old zebrafish [45-50]. However, animals eventually develop immune responses and kill engrafted cells—preventing analysis of animals after 7 days of life. Moreover, only 20-200 cells can be implanted into larval fish due to their small size. The next generation of cell transplantation utilized transient ablation of the immune system by gamma-irradiation, allowing robust engraftment of tumor and hematopoietic cells for up to 20 days post-transplantation where in excess of 1×10$^6$ cells can be implanted per fish (FIG. 2) [39, 51]. However, the recipient immune system recovers by 30 days post-irradiation and attacks the graft leading to rejection. Recent experiments have shown robust blood cell engraftment into myb-deficient fish that lack fully functional blood stem cells [52], Although powerful for study of blood development, myb mutant fish die in early adulthood and are not amenable to adoptive transfer of other cell types. Work from the Klemke laboratory has shown that immune suppression by dexamethasone permits engraftment of a wide variety of human tumors to time points exceeding 30 days [53], strongly arguing that human cancer can survive and grow in adult fish. However, these protocols result in only partial immune suppression through impairment of lymphocyte function, require constant dosing of drugs, and would not be useful for assessment of hematopoietic and leukemia cell engraftment. Finally, syngeneic strains of zebrafish facilitate robust and large-scale engraftment studies using fluorescent-labeled zebrafish cells [35-38]. These models require that donor and recipients are both in the same strain and engraftment of mammalian cells into these models is not possible as they are not immune compromised. To date, immune compromised zebrafish have yet to be used for universal cell transplantation of either zebrafish or mammalian cells.

Genome Engineering and Creation of Mutant Zebrafish

Robust methods to induce targeted gene disruption in zebrafish using zinc finger nucleases (ZFNs) and Transcription Activator-Like Effector Nucleases (TALENs) have been developed [54-65].

ZFNs consist of an engineered array of zinc fingers fused to the non-specific FokI nuclease domain and function as dimers to introduce targeted DNA double-strand breaks (DSBs). Each zinc finger binds to approximately three base pairs (bps) of DNA and a ZFN monomer commonly utilizes three to six zinc finger motifs to bind 9-18 by target DNA. See, e.g., Miller et al., 1985, EMBO J., 4:1609; Berg, 1988, Proc. Natl. Acad. Sci. USA, 85:99; Lee et al., 1989, Science. 245:635; and Klug, 1993, Gene, 135:83; Rebar et al., 1994, Science, 263:671; Choo et al., 1994 Proc. Natl. Acad. Sci. USA, 91:11163; Jamieson et al., 1994, Biochemistry 33:5689; Wu et al., 1995 Proc. Natl. Acad. Sci. USA, 92: 344; Segal et al., 2003, Biochemistry, 42:2137-48; Beerli et al., 2002, Nat. Biotechnol., 20:135-141; Mandell et al., 2006, Nucleic Acids Res., 34:W516-523; Carroll et al., 2006, Nat. Protoc. 1:1329-41; Liu et al., 2002, J. Biol. Chem., 277:3850-56; Bae et al., 2003, Nat. Biotechnol., 21:275-280; Wright et al., 2006, Nat. Protoc., 1:1637-52. Combinatorial selection-based methods that identify zinc finger arrays from randomized libraries have been shown to have higher success rates than modular assembly (Maeder et al., 2008, Mol. Cell, 31:294-301; Joung et al., 2010, Nat. Methods, 7:91-92; Isalan et al., 2001, Nat. Biotechnol., 19:656-660). In preferred embodiments, the zinc finger arrays are described in, or are generated as described in, WO 2011/017293 and WO 2004/099366. Additional suitable zinc finger DBDs are described in U.S. Pat. Nos. 6,511,808, 6,013,453, 6,007,988, and 6,503,717 and U.S. patent application 2002/0160940.

By contrast, TALENs bind to DNA through a highly conserved 34 amino acid transcription activator-like effector (TALE) repeat domain found in the plant pathogen Xanthomonas. Each TALE repeat domain binds to a single by of DNA with specificity determined by two amino acids—known as the repeat variable di-residues (RVDs). TALEs can be joined together into extended arrays to create proteins that bind longer stretches of DNA sequence. TALE repeats are fused to the FokI nuclease domain and cleave DNA as a dimer. Methods for creating and using TALENs are well known in the art, see, e.g., Reyon et al., Nature Biotechnology 30,460-465 (2012); as well as the methods described in Bogdanove & Voytas, Science 333, 1843-1846 (2011); Bogdanove et al., Curr Opin Plant Biol 13, 394-401 (2010); Scholze & Boch, J. Curr Opin Microbiol (2011); Boch et al., Science 326, 1509-1512 (2009); Moscou & Bogdanove, Science 326, 1501 (2009); Miller et al., Nat Biotechnol 29, 143-148 (2011); Morbitzer et al., T. Proc Natl Acad Sci USA 107, 21617-21622 (2010); Morbitzer et al., Nucleic Acids Res 39, 5790-5799 (2011); Zhang et al., Nat Biotechnol 29, 149-153 (2011); Geissler et al., PLoS ONE 6, e19509 (2011); Weber et al., PLoS ONE 6, e19722 (2011); Christian et al., Genetics 186, 757-761 (2010); Li et al., Nucleic Acids Res 39, 359-372 (2011); Mahfouz et al., Proc Natl Acad Sci USA 108, 2623-2628 (2011); Mussolino et al., Nucleic Acids Res (2011); Li et al., Nucleic Acids Res 39, 6315-6325 (2011); Cermak et al., Nucleic Acids Res 39, e82 (2011); Wood et al., Science 333, 307 (2011); Hockemeye et al. Nat Biotechnol 29, 731-734 (2011); Tesson et al., Nat Biotechnol 29, 695-696 (2011); Sander et al., Nat Biotechnol 29, 697-698 (2011); Huang et al., Nat Biotechnol 29, 699-700 (2011); and Zhang et al., Nat Biotechnol 29, 149-153 (2011); all of which are incorporated herein by reference in their entirety.

The DSBs induced by either ZFNs or TALENs are repaired by non-homologous end joining (NHEJ)—an error-prone process that results in the creation of insertion or deletion mutations (indels) that can shift the frame and lead to premature translation termination. Using targeted genomic engineering approaches, DNA mutations have been successfully targeted within somatic cells of zebrafish [for a review see 84]; some of these have produced heritable loss-of-function mutations; see, e.g., [54, 56-67], all of which are incorporated herein by reference in their entirety.

Fish

A wide variety of fish species, including teleosts, can be utilized to generate the immune-compromised genetically-modified fish disclosed herein. Suitable teleosts include, e.g., zebrafish (*Danio rerio*); medaka (*Oryzias latipes*); mummichog (*Fundulus heteroclitus*); killifish (Genus *Fundulus*); catfish (Genus *Ictalurus*), such as channel catfish; carp (Genus *Cyprinus*), such as common carp; puffer fish (*Tetraodontidae*); and trout or salmon (such as Genus *Salvelinus, Salmo*, and *Oncorhynchus*). In some embodiments, the fish models are transparent or translucent in one or more of the following stages: the embryonic, larval, or adult stage.

Zebrafish offer important advantages over other fish models. The genetic makeup of zebrafish is closely related to other vertebrates, including human and mouse, thus zebrafish serves as an excellent model for the study of vertebrate development and human diseases. Zebrafish share with mammals major lymphoid organs such as thymus and gut-associated lymphoid tissues. Although zebrafish do not possess lymph nodes or bone marrow, the species maintains a major hematopoietic activity in the kidney. Various zebrafish strains can be used to generate the immune-compromised genetically-modified fish. Suitable zebrafish strains include the wild-type strains such as AB, Tübingen, AB/Tübingen, Sanger AB Tübingen, SJD, SJA, WIK strains, and the pigmentation mutant strains such as golden, albino, rose, panther, leopard, jaguar, puma, bonaparte, cezanne, chagall, dali, duchamp, picasso, seurat, sparse, shady, oberon, opallus, nacre, roy, and (preferably) Casper strains.

Adult wild-type zebrafish have three classes of pigment cells arranged in alternating stripes: black melanophores, reflective iridophores, and yellow xanthophores (FIG. 1a). The pigmentation mutant strains harbor one or more mutations in the genes that play important roles in the development of melanophores, iridophores, or xanthophores. For example, the golden mutant zebrafish harbors a point mutation in the s1c24a5 gene and has diminished number, size, and density of melanosomes (Lamason et al., Science 310 (5755):1782-6, 2005). Similarly, the albino mutants also have a mutation in the s1c24a5 gene and show very light body pigmentation (see, e.g., Lamason et al., Science. 310. (2005): 1782-86). The rose mutants harbor a mutation in the endothelin receptor b1 (ednrb 1) gene and have fewer numbers of melanocytes and iridophores during pigment pattern metamorphosis and exhibit disrupted pattern of the melanocytes (Parichy et al., Dev. Biol. 227(2):294-306, 2000).

Several zebrafish mutant strains completely lack one or more classes of pigment cells. The panther mutants complete lack xanthophores and have fewer melanophores due to a mutated fms (M-CSF receptor) gene (Parichy et al., Development 127: 3031-3044, 2000). The nacre mutant of zebrafish completely lacks melanocytes due to a mutation in the mitfa gene (Lister et al., Development 126:3757-3767, 1999). The roy orbison (roy) zebrafish is a spontaneous mutant with unknown mutations, which cause a complete lack of iridophores, sparse melanocytes, and a translucency of the skin. The roy mitfa$^{-/-}$ mutant zebrafish designated "Casper" shows a complete loss of all melanocytes and iridophores [34]. The body of Casper fish is almost entirely transparent during both embryogenesis and adulthood, and the internal organs, including the heart, aorta, intestinal tube, liver, and gallbladder, can be seen using standard stereomicroscopy (FIG. 1b). In female Casper fish, individual eggs are also observable. The Casper mutant zebrafish is entirely viable, with incrossed adults producing large numbers of viable offspring at expected mendelian ratios and no heterozygous phenotype [34]. By utilizing the optically clear Casper strain fish, engraftments in the fish can be directly visualized through the use of reporter dyes or proteins by a variety of detection techniques, e.g., light microscopy, fluorescence microscopy, colorimetry, chemiluminescence, digital imaging, microplate reader techniques, and in situ hybridization. Therefore, the Casper strain fish is particularly suitable for the experiments disclosed herein.

Immune-Related Genes

The genetically modified fish described herein have germline mutations in one or more immune-related genes that render their immune systems less active than wild type. In some embodiments, their immune systems are inactive. In some embodiments, the fish lack one or more of T, B, and/or NK cells, or have inactive T, B, and/or NK cells. The immune-related genes that are inactivated in the fish described herein include one or more of foxn1, rag2, jak3, Il2rga, Il2rgb; and prkdc. In some embodiments, the mutations are as shown in FIG. 3 or 5.

foxn1

The transcription factor forkhead box N1 (foxn1) is required for the immigration of thymocyte precursors into thymic primordium. Mutation of foxn1 gene leads to nude phenotype characterized by disrupted T-lymphopoiesis, athymia, and hairlessness in human, mouse and rat [31]. The zebrafish casanova mutants lack the zebrafish homolog of foxn1 gene and show impaired endodermal formation [31]. The sequences of mRNA, genomic DNA, and protein of zebrafish foxn1 are known in the art and their GenBank Reference Numbers are listed in the table below.

| foxn1 | GenBank Reference No. |
|---|---|
| mRNA | Accession: NM_212573.1 GI: 47086884 |
| Genomic DNA | Accession: NC_007126.5 GI: 312144715 |
| Protein | Accession: NP_997738.1 GI: 47086885 | rag2

The recombination-activating gene 2 (rag2) encodes a protein that is involved in the initiation of V(D)J recombination during B and T cell development. The protein RAG-2 forms a complex with RAG-1, and this complex cleaves DNA at conserved recombination signal sequences and forms double-strand breaks in DNA. Both RAG-1 and RAG-2 are essential to the generation of mature B and T lymphocytes. The rag1 mutant zebrafish are able to reach adulthood and are fertile [33]. The sequences of mRNA, genomic DNA, and protein of zebrafish rag2 are known in the art and their GenBank Reference Numbers are listed in the table below.

| rag2 | GenBank Reference No. |
|---|---|
| mRNA | Accession: NM_131385.2 GI: 119943149 |
| Genomic DNA | Accession: NC_007136.5 GI: 312144705 |
| Protein | Accession: NP_571460.2 GI: 119943150 |

Preferably, the rag2 mutation is hypomorphic, i.e., results in alleles that are only partially inactive (similar to the mutations associated with human Omenn syndrome). See e.g., FIG. 5.

jak3

The Janus kinase (JAK) family of tyrosine kinases mediates intracellular signal transduction in response to cytokines Jak3 is predominantly expressed in immune cells and is associated with the interleukin-2 receptor gamma chain (Il2rg), a component of the receptors for IL-2, IL-4, IL-7, IL-9, IL-15, and IL-21. Jak3-deficient mice have profound reductions in thymocytes and severe B cell and T cell lymphopenia similar to severe combined immunodeficiency disease (SCID), and the residual T cells and B cells are functionally deficient [29]. Nonsense mutations in the zebrafish homologs of JAK1 and JAK3 preferentially affect T cell development [32]. The sequences of mRNA, genomic DNA, and protein of zebrafish jak3 are known in the art and their GenBank Reference Numbers are listed in the table below.

| jak3 | GenBank Reference No. |
|---|---|
| mRNA | Accession: XM_002663087.2 GI: 326669955 |
| Genomic DNA | Accession: NC_007119.5 GI: 312144722 |
| Protein | Accession: XP_002663133.2 GI: 326669956 |

Il2rga/Il2rgb

The interleukin-2 receptor gamma chain (Il2rg) is an important signaling component of many interleukin (IL) receptors, including receptors for IL-2, IL-4, IL-7, IL-9, IL-15, and IL-21, and is thus referred to as the common gamma chain. Deletion of Il2rg in the NOD/SCID mice results in lack of functional lymphocytes and nature killer (NK) cells. The sequences of mRNA, genomic DNA, and protein of zebrafish Il2rga and Il2rgb are known in the art and their GenBank Reference Numbers are listed in the table below.

| | GenBank Reference No. |
|---|---|
| Il2rga | |
| mRNA | Accession: NM_001128271.1 GI: 190194257 |
| Genomic DNA | Accession: NC_007121.5 GI: 312144720 |
| Protein | Accession: NP_001121743.1 GI: 190194258 |
| Il2rgb | |
| mRNA | Accession: NM_001123050.1 GI: 176866336 |
| Genomic DNA | Accession: NC_007125.5 GI: 312144716 |
| Protein | Accession: NP_001116522.1 GI: 176866337 | prkdc

The DNA-dependent protein kinase catalytic subunit (prkdc) gene encodes the catalytic subunit of the DNA-dependent protein kinase (DNA-PK). DNA-PK functions with the Ku70/Ku80 heterodimer protein in DNA double strand break repair and recombination. Defective DNA-PK activity is linked to V(D)J recombination defects and DNA repair defects associated with the murine SCID mutation [20]. The sequences of mRNA, genomic DNA, and protein of zebrafish prkdc are known in the art and their Genbank Reference Numbers are listed in the table below.

| prkdc | GenBank Reference No. |
| --- | --- |
| mRNA | Accession: XM_001919553.2 GI: 326669530 |
| Genomic DNA | Accession: NC_007118.5 GI: 312144723 |
| Protein | Accession: XP_001919588.2 GI: 326669531 |

The fish described herein can also have combinations of these mutations, e.g., foxn1, rag2, jak3, prkdc; and interleukin 2-receptor gamma a and b (IL2RGa and IL2RGb). For example, foxn1 and rag2; foxn1 and jak3; foxn1 and Il2rga; foxn1 and Il2rgb; or foxn1 and prkdc; rag2 and jak3; Il2rga; rag2 and Il2rgb; rag2 and prkdc; jak3 and Il2rga; jak3 and Il2rgb; jak3 and prkdc; Il2rga and Il2rgb; Il2rga and prkdc; foxn1, rag2, and jak3; foxn1, rag2, and Il2rga; foxn1, rag2, and Il2rgb; foxn1, rag2, and prkdc; foxn1, jak3, and Il2rga; foxn1, jak3, and Il2rgb; foxn1, jak3, and prkdc; foxn1, Il2rga and Il2rgb; foxn1, Il2rga and prkdc; foxn1, rag2, jak3, and Il2rga; foxn1, rag2, jak3, and Il2rgb; foxn1, rag2, jak3, and prkdc; foxn1, rag2, jak3, Il2rga or Il2rgb, and prkdc; rag2, jak3, and Il2rga or Il2rgb; rag2, jak3, and prkdc; Il2rga and/or Il2rgb and prkdc; rag2, jak3, Il2rga and/or Il2rgb, and prkdc; or any other subcombination of two, three, four, five, or all six of foxn1, rag2, jak3, prkdc; and IL2RGa and/or IL2RGb.

Methods of Use

The fish described herein can be used, e.g., in stem cell biology, regenerative medicine, and cancer research. Fish facilitate large-scale transplantation experiments at greatly reduced costs to investigators. For example, 350+ adult zebrafish transplant experiments can be performed daily by a single investigator [35-38, 68]. Fish can also be engrafted at early stages of development beginning from the one cell stage of life on into adulthood. Such experiments further enhance the scale of experimentation due to reduction in animal size of larval fish permitting raising animals in 48-well formats in lowered amounts of water. Moreover, fish, e.g., zebrafish, can be housed and maintained at very low cost. In embodiments utilizing optically clear fish, e.g., the Casper strain zebrafish, engraftment can be directly visualized, e.g., through the use of fluorescent reporter dyes and proteins. Primary engrafted human and mouse tumors can often be directly visualized as masses, especially in the translucent Caspar strains of fish given that internal zebrafish organs can be seen, facilitating tracking of human and mouse cells directly without dye or transgene labeling.

As described herein, the ability to create targeted gene mutations in zebrafish using ZFNs and TALENs e.g., as described in [58, 64], can be used to effectively create zebrafish gene modifications that mimic mutations found in human and mouse SCID. Zebrafish can also be raised at 35-37° C. mimicking the temperatures seen in mouse and human, thus immune compromised fish will likely provide new experimental models for adoptive transfer of human and mouse cells to assess cell function and regenerative capacity. The use of large numbers of engrafted animals along with chemical screening approaches will likely revolutionize the types and scale of experiments that can be completed to assess mouse and human cellular functions—identifying the next generation of drugs to treat a variety of developmental, age-related, and cancer diseases.

The use of zebrafish for xenograft cell transplantation to assess stem cell phenotypes, regenerative capacity, and malignancy has lagged behind mouse models due in large part to the lack of immune compromised zebrafish. As described herine, ZFN and TALEN technology have been used for targeted gene inactivation in zebrafish [58, 64]. The present inventors have created TALENS and ZNFs that target endogenous genes for rag2, foxn1, prkdc, jak3, and il2rg. These mutations are engineered within the protein to create full-loss-of-function alleles or in some cases, hypomorphic alleles that are only partially inactive (e.g., in the case of rag2). The development of immune compromised zebrafish defective in these genes will facilitate large-scale transplantation experiments and robust methods for assessing cellular function, e.g., the cellular functions of normal stem cells and malignant cells.

The immune compromised genetically-modified fish disclosed herein can be used as transplant recipients to assess stem cell phenotypes, regenerative capacity and malignancy. In some embodiments, the stem cells are isolated from a donor zebrafish under sterile conditions. The donor fish can be treated with antibiotics and then euthanized, and the skin of the fish can be removed. The deskinned donor fish can then be briefly rinsed in bleach and homogenized, and cells of the donor fish can be purified, e.g., by Ficoll gradient, to eliminate bacteria and fungus. The cells of interest can be isolated and injected into the immune compromised genetically-modified fish disclosed herein. Transplanted fish can be examined using a variety of detection techniques, e.g., light microscopy, fluorescence microscopy, colorimetry, chemiluminescence, digital imaging, microplate reader techniques, and in situ hybridization. Some embodiments utilize zebrafish to zebrafish transplantations that can be used, e.g., to assess regenerative capacity of muscle, blood, liver, kidney cells, pancreas (including b-cells), skin, retinal cells, germ cells, and other regenerative tissues. Moreover, immune compromised fish can be used for cross-species engraftment of cells, e.g., normal cells, from other fish species as well as cancer. In all instances, genetic and chemical approaches can be used to assess effects on regeneration and tumor growth—providing rapid methods to identify critical pathways that drive regeneration and cancer growth.

Regeneration of the immune system can be studied, e.g., using fluorescent protein labeled hematopoietic stem cells (HSC). Since the kidney marrow is the site of hematopoiesis in zebrafish and contains the HSC cells, GFP-expressing kidney marrow cells can be isolated, e.g., from adult ubiquitin-GFP transgenic (Mosimann et al., Development. 2011 January; 138(1):169-77) and/or blood-specific promoter-GFP transgenic (Ellett et al., Blood Jan. 27, 2011 vol. 117 no. 4 e49-e56; Lam et al., Blood. 2009 Feb. 5; 113(6):1241-9) zebrafish kidneys and used for transplantation. Briefly, the donor zebrafish can be anesthetized and the kidneys can be dissected out under sterile conditions and placed into ice-cold sterile PBS buffer containing 5% fetal calf serum. Whole kidney marrow cell suspensions can be generated by aspiration followed by passing through a 40-μm nylon mesh filter. DnaseI and heparin can be added to lessen aggregation. The transplant recipient fish can be irradiated several days prior to transplant. Cells, e.g., approximately $1.5 \times 10^6$ whole kidney marrow cells, e.g., in 5 ul volume, can be transplanted into each anesthetized recipient fish by retro-orbital injection as described before (Pugach et al., J Vis Exp 34:1645, 2009). The transplanted fish can be examined weekly under an inverted fluorescent microscope to monitor regenerative capacity of HSCs based on the distribution of GFP-expressing cells in the thymus, kidney, spleen, and other organs. Imaging of the transplanted fish can be captured using a digital camera. Fish can be sacrificed and GFP-expressing cells can be isolated from the kidney marrow, thymus, and spleen, and the cell lineages can be analyzed by fluorescence-activated cell sorting (FACS) and Wright-Giemsa/May-Grunwald staining Successful engraftment can be defined by long-term and sustained GFP-positivity in all blood cell lineages. Loss of GFP-expressing cells in the blood denotes rejection, indicating the recipient fish is not immune compromised.

Regenerative capacity of muscle stem cells can be studied, e.g., using fluorescent protein labeled muscle stem cells. For example, muscle cells can be isolated from adult alpha-actin-RFP transgenic zebrafish utilizing the sterile techniques described above. A small amount of a toxin, e.g., snake venom (cardiotoxin) can be injected into the dorsal musculature of the genetically-modified recipient fish to damage the muscle fibers and trigger regeneration. Alternatively, muscle cell engraftment can be performed without pre-injury. Approximately $5 \times 10^4$ RFP-expressing muscle cells, including muscle stem cells, can be injected into the dorsal musculature, at the same location as any pre-injury. The transplanted fish can be examined by fluorescent stereomicroscope to monitor the regenerative capacity of the muscle stem cells based on the distribution of RFP-expressing cells at the dorsal musculature of the fish.

In some embodiments, the genetically-modified fish disclosed herein can be used in cancer research. For example, GFP or RFP expressing mammalian tumor cells can be transplanted into the immune compromised genetically-modified zebrafish and tumor development can be directly visualized. Exemplary mammalian tumor cells include various sarcoma, carcinoma, adenocarcinoma, melanoma, and leukemia cell lines. About $1 \times 10^6$ sterile tumor cells in 10 ul can be implanted into the peritoneal cavity of a recipient genetically-modified fish. Transplanted fish can be raised in transparent flasks at 35-37° C. under sterile conditions and can be examined, e.g., by fluorescent stereomicroscope, to monitor tumor growth in vivo. Tumors also need not be fluorescently tagged if they are engrafted into optically clear, Casper strain fish where tumors can be directly visualized.

The genetically-modified fish transplanted with mammalian tumor cells are useful to screen for therapeutic compounds that modulate tumor formation. The genetically-modified fish transplanted with tumor cells can be exposed to a test compound or a control substance. Tumor growth in the genetically-modified fish exposed to the test compound can be compared with the tumor growth in the genetically-modified fish exposed to the control substance. If a test compound suppresses or decreases tumor growth in the fish, it is identified as a candidate therapeutic compound; optionally the compound is selected and further assays can be conducted using the selected compound. The test compounds can be administered to the genetically-modified fish directly by microinjection, or added to the water holding the genetically-modified fish, with the fish taking up the compound through their skin, gills, and gut. Thus a method of identifying a candidate therapeutic compound for the treatment of a mammalian tumor is provided by the present disclosure. The method includes transplanting cells from a mammalian tumor into the genetically-modified fish disclosed herein; contacting the fish with a test compound; evaluating the growth of the mammalian tumor cells in the presence of the test compound; comparing the level of growth of the mammalian tumor cells in the presence of the test compound to a reference level; and identifying a compound that decreases the level growth of the mammalian tumor cells as a candidate therapeutic compound. In some embodiments, the mammalian tumor cells are derived from a subject with cancer. In this way the fish can be used as a model to assess primary tumor responses to combined known therapies and for stratification into clinical trials—identifying primary patient samples that best respond to therapies for the treatment of patients. In some embodiments, the identified candidate therapeutic compound is administered to the subject with cancer. Human and mouse primary cancers and cancer cell lines can be engrafted into immune compromised fish lines throughout development and into adult stages.

In some embodiments, the genetically-modified fish, e.g., transplant recipient fish, can be raised under sterile condition, optionally in the presence of one or more antibiotics and antifungals, e.g., Tetracycline, penicillin, fungazone, Cipro (Ciprofloxacin), bacitracin, and/or gentamycin.

In some embodiments, mammalian cells are transplanted into the fish, and before or after the transplant procedure the temperature of the fish container can be increased slowly, e.g., 0.75° C. daily, from 26.5° C. to 37° C. For example, intended transplant recipients can be acclimated to 35-37° C. for several days prior to engraftment with human or mouse cells.

The fish described herein, e.g., the zebrafish lines, can also be used to evaluate totipotency of stem cells, e.g., human, mouse, and other mammalian ES, iPS, and pluripotent cells. In these examples, investigators can engraft ES or modified cells into the fish and assess teratoma formation—a surrogate for pluripotency. The fish can be contacted with various test compounds, e.g., to discover drug combinations or genetic manipulations that alter cell fate. Teratoma assays are the gold standard for potency. The effects of the test compounds can also be evaluated. See, e.g., Science. 2003 Feb. 7; 299(5608):887-90.

For example, in some embodiments endogenous tissue-restricted, pluripotent stem cells (e.g., embryonic stem cells), or induced-pluripotent stem cells (iPSC), which can be, e.g., isolated from culture or in vivo, are purified and microinjected into fish. The stem cells can be placed into various locations in the fish including but not limited to the peritoneum, the vessels of the eye, the muscle, and various visceral organs. Drugs or genetic modifications (e.g., siRNA, antisense, or transgenes), e.g., drugs or genes that modulate specific pathways, can be delivered to the fish, and assessed for functional effects on growth or differentiation of the stem cells and their progeny using standard techniques including visualization of cells in vivo, sectioning and staining, etc. In some embodiments, the stem cells are labeled in some way, e.g., they express a fluorescent protein, so that the stem cells and their progeny are readily detectable.

EXAMPLES

The invention is further described in the following examples, which do not limit the scope of the invention described in the claims.

Example 1. Mutant Zebrafish Deficient for Genes of Interest

We have previously described the efficient gene inactivation of the jak3 and rag2 loci in zebrafish through ZFN technology [58, 64]. ZFNs were engineered to induce targeted gene mutation in jak3 (near amino acid P368) and rag2 (near amino acid G448) at rates of 1.4% and 7.7%, respectively, in embryos [58]. ZFNs pairs were microinjected as RNA into one-cell stage embryos and assessed for somatic DNA mutation rates at 3 days of life. ZFN mutations often lead to frame-shift mutation and premature stop codons that create truncated proteins similar to those found in mouse and human SCID (listed in FIG. 4).

Described herein are TALENs that disrupt foxn1, prkdc, and il2-receptor gamma (both isoforms, FIG. 3). Somatic mutation frequencies were exceedingly high using TALENs to these genes, with somatic DNA mutation rates ranging from 6.0%-45.5%. Foxn1 mutations were induced at the ATG start site and are hypothesized to result in loss-of-function phenotypes based on the mutational spectrum observed in mouse and human SCID (FIG. 4) [69-71]. Il2-receptor gamma mutations were targeted near amino acid residues mutated in human SCID (C62X and K97X) [72] at zebrafish residues N31 and R92, respectively for each duplicated allele. Il2rg is duplicated in zebrafish, requiring inactivation of both homologues. Finally, TALENs were created that target prkdc at amino acid D3601 to create a mutation that ablates the kinase domain. Similar mutations resulted in complete loss of Prkdc function in dog (E3627X), resulting in SCID [73, 74]. The SCID puppies were susceptible to bacterial and viral infections and rarely survived past 3-4 months of age when raised in conventional environments [73]. We have created the first generation of TALEN reagents to successfully induce indel mutations within all six genes outlined in this proposal.

The transgenic fish were made as follows: one-cell stage zebrafish were injected with TALENs or ZFNs and raised to adulthood (n=100 F0 adult fish were raised per ZFN or TALEN pair). Adult F0 fish were incrossed and genomic DNA was isolated from 12 individual progeny from each cross. PCR was used to amplify the target region and purified fragments were sequenced. Because ZFNs and TALENs induce insertion and deletion mutations (indels), sequencing can easily identify heterozygous mutant animals. These experiments identified F0 founder fish that were capable of producing offspring with mutated genes. Subsequently, F1 animals were raised to adulthood, fin clipped, and mutations verified by sequencing.

Once mutant lines have been established, heterozygous adult fish are incrossed and resulting progeny raised under one of two conditions. First, fish are raised under normal laboratory conditions without any antibiotic treatment. Importantly, the jak3 and rag2 mutant fish described herein survive as homozygous adult fish raised under conventional laboratory rearing.

As needed, fish are raised under germ-free conditions. Specifically, fertilized embryos are derived germ-free (GF) through exposure to antibiotics, iodine, and bleach using established protocols [75, 76]. GF embryos are raised to adulthood in Gnotobiotic Zebrafish Medium supplemented with antibiotics in sterile plastic vented flasks [75] to eliminate microbial exposure, containing autoclaved activated carbon to promote water quality. Partial media changes are performed manually, e.g., 2-3 times per week, and sterility tests are performed using established techniques. GF animals are fed a combination of Zeigler Zebrafish Diet (Zeigler Brothers Inc.) sterilized by radiation (Neutron Products Inc.) and axenic brine shrimp. These approaches have permitted the rearing of germ-free fish lines to adult stages (see Rawls et al., Cell 127(2): 423-33. (2006)). Rearing in germ-free conditions does not impact overall survival of fish (FIG. 6) [77]. To date, we have been able to rear the fish to adulthood using standard zebrafish husbandry techniques, supporting that immune compromised fish will be viable and able to be maintained as conventional stocks.

We have now identified F0 founder animals that produce offspring that harbor inactivating mutations in foxn1, il2gra, and il2grb (FIGS. 5A-5B). We have opted to make additional Il2gra lines because some lines had only amino acid deletions rather than frame shift or early termination codons (Table 1). We have identified more than 6 alleles for each gene in F1 progeny and are now growing these animals up in our facility (FIG. 5B).

Table 1 lists the immune compromised zebrafish strains created to date using Zinc Finger Nuclease (ZFNs) and TALEN mutagenesis approaches. Only lines with adult F1 animals are shown. Frame shift stop (fs). Deletion (D or del). Asterisks indicate lines with homozygous adult mutant fish.

TABLE 1

| Gene | Line | Strain | nt mutation | AA change |
|---|---|---|---|---|
| rag2 | #14 | AB* | D3 + 2 | E450fs |
|  | #14 | Casper* | D3 + 2 | E450fs |
|  | 6C | AB | D20 + 36 | S447fs |
| jak3 | #7.8 | AB* | D10 | P368fs |
|  | #7.8 | Casper | D10 | P368fs |
|  | #1 | AB* | D10 + 18 | P369fs |
|  | #1 | Casper | D10 + 18 | P369fs |
| foxn1 | NA | Casper* | D1 | G7fs |
| prkdc | QT1 | Casper* | D8 | D3612fs |
| il2rga | #1 | Casper | D6 | D93_D94del |
|  | #2 | Casper | D9 | R92_D94del | a) $rag2^{E450fs}$—Creation of a Hypomophic rag2 Mutant Line (Also Noted Herein as rag2 Line 14)

In addition, zinc finger nucleases were designed to target the plant homeodomain finger (PHD domain) of the zebrafish rag2 gene at similar, but not identical, residues commonly mutated in Omenn Syndrome ($rag2^{E450fs}$, FIGS. 4A-K, FIG. 5A (Line 14)). Mutations in residues of the PHD domain disrupt the RAG2 protein interaction with trimethylated histone H3 to alter chromatin accessibility and to partially impair V(D)J recombination in vivo. Heterozygous $rag2^{E450fs}$ mutant fish were incrossed and raised to adulthood. Animals were genotyped at 3 months of age, revealing expected Mendelian ratios (146:wild type, 265:heterozygous, and 129:$rag2^{E450fs}$ mutant). Histological analysis of 90-day-old $rag2^{E450fs}$ mutant zebrafish revealed a striking reduction in thymic T cells and thymic involution (FIGS. 4c,d,f,g) reminiscent of what is commonly observed in T cell deficient lines of mice. Analysis of whole kidney marrow revealed that adult homozygous $rag2^{E450fs}$ zebrafish contained all blood cell lineages (FIGS. 4e,h); however, quantization showed a striking 75% reduction in lymphocytes in $rag2^{E450fs}$ mutant zebrafish when compared to age-matched, wild type siblings (FIG. 4i). Gene expression analysis of whole kidney marrow showed reduced transcript expression for the mature B and T cell markers, lck, tcra, tcrb, igm (FIG. 4j). By contrast, rag1 transcript levels were not reduced in the marrow of mutant animals suggesting that early B cell precursors were not altered in $rag2^{E450fs}$ mutant zebrafish (FIG. 4j). mpx and lcpl markers for neutrophils, monocyte/macrophages, and other cell lineages were not altered in $rag2^{E450fs}$ mutant zebrafish (FIG. 4j). We have now bred our $rag2^{E450fs}$ mutant zebrafish into the Caspar strain of fish and have developed optically clear, immune compromised animals and have working on a publication demonstrating the utility of this model for studying normal stem cell engraftment and imaging the hallmarks of cancer initiation and progression.

b) jak3$^{P369fs}$ and jak3$^{P368fs}$ Mutant Animals

We have identified two independent lines with mutations in jak3. Both lines exhibit robust reductions in thymic T cells in homozygous animals. These animals are now being characterized to identify specific cell types affected by jak3 loss as shown in FIG. 3. Remarkably, these fish lines are viable as homozygous fish and robustly engraft zebrafish tissues and cancer. These animals are currently being assessed for engraftment of human cancer cells.

c) foxn1$^{G7fs}$ Mutant Animals

We have identified a single mutant line that harbors a foxn1$^{G7fs}$ mutation. Sadly, homozygous mutant fish did not show a reduction in thymic T cells as would be expected based on the mouse knockouts. Moreover, these fish lines failed to engraft fluorescent-labeled T-ALL, suggesting that they are not immune compromised (data not shown). We suspect that an alternative ATG is used to create a functional protein and thus, this mutation does not cause a phenotype in mutant animals. We have redesigned TALENs to the K220 amino acid, at similar amino acid residues found in NUDE mice. These new TALEN pairs can induce indel mutations at the specified target site and F0 fish are now being screened for the ability to produce mutant offspring (see below).

d) prkdc$^{D3612fs}$ Mutant Animals

We have identified a single mutant line that harbors a prkdc$^{D3612fs}$ mutation. We are currently in the earliest phases of characterizing this mutant line. Homozygous mutants are viable and survive in normal zebrafish rearing conditions. These animals are now being characterized to identify specific cell types affected by prkdc loss as shown in FIG. 3 and are being assessed for engraftment ability.

To verify the functional consequences of foxn1, rag2, jak3, and prkdc homozygous loss in mutant zebrafish, each homozygous mutant line was assessed for altered T-cell specification and loss by performing fluorescent in situ hybridization for rag1 and lymphocyte-specific protein kinase (lck) at 5dpf. Importantly, published experiments have established roles for foxn1, rag2, and jak3 in T-cell development, with loss of gene function resulting in severely reduced numbers of thymocytes at 5 days of life [31-33]. Similar results have now been documented in the jak3-deficient line described herein (line #7.8, FIG. 7).

Whole kidney marrow is also isolated from homozygous adult zebrafish and assessed for Tcr-beta receptor rearrangements utilizing a PCR-based approach to detect each of the unique 102 possible receptor combinations (rag2 and prkdc loss should impair V(D)J recombination) [36]. IgM receptor rearrangement and expression will also be assessed in whole kidney marrow as previously described [78, 79] establishing a role for rag2 and prkdc in modulating B cell development and function. NK cell functional assays are used to assess a role for il2rg and jak3 in regulating NK cell activity in zebrafish. To date, markers for NK cells have yet to be fully described in the zebrafish. Given that Il2rg has been duplicated in fish, double homozygous mutant animals are also assessed for phenotypes as outlined above. These experiments will demonstrate that gene mutations exert important and conserved roles in T, B, and NK cell function.

As demonstrated herein, homozygous rag2-deficient zebrafish are viable, survive to adulthood, can be genotyped by fin clip, and engraft a wide range of cell types (FIGS. 8, 9, 11, 13, 14). jak3 homozygous mutant fish survive at correct Mendelian ratios under normal laboratory conditions to 4 months of age, yet routinely die 2-3 days following fin clip—suggesting infection can kill these animals. In this case, raising fish in GF conditions may be required. We also note that rag1 and jak3 mutant zebrafish have been created by ENU-mutation and TILLING approaches and are viable as homozygous adults [32, 33], but have yet to assessed for transplant engraftment.

Mutations induced by ZFNs and TALENs should result in observable cellular phenotypes. For example, morpholino knockdown of foxn1 and gene knockout of jak3 and rag1 has been shown to result in severe reductions in thymocytes at 5 dpf. As expected, homozygous mutant jak3 fish lack thymocytes at 5 days of life (FIG. 7). Moreover, rag2 and jak3 mutant zebrafish robustly engraft normal stem cell and malignant tumors as adults for up to 45 days post-transplant (FIGS. 8, 9, 11, 13, and 14), suggesting prominent roles for these genes in regulating immune cell function.

Example 2. Engraftment of Zebrafish Fluorescent-Labeled T-Cell Leukemias

Initial experiments focused on adoptive transfer of dsRED+ or GFP+ leukemias into recipient lines due to 1) the ease of generating fluorescent-labeled leukemias with known leukemia propagating cell frequency, 2) the large number of cells that can be harvested from a single fish ($1 \times 10^8$ cells), and 3) the leukemias are rejected by the same mechanisms as normal, non-malignant cells (FIG. 2) [35, 36, 38, 79, 80].

Fluorescent-labeled T-cell acute lymphoblastic leukemia (T-ALL) cells were isolated from leukemic CG1-strain or AB-strain zebrafish. Specifically, the leukemic fish were euthanized and homogenized in sterile 0.9×PBS supplemented with 5% FBS in a cell culture hood. T-ALL cells were implanted into the peritoneum of 90 day old 1) rag2−/− (homozygous rag2$^{E450fs}$, line 14 fish), and 2) jak3−/− single mutant fish (line 7.8) ($1 \times 10^5$ cells/fish, n=3 individual T-ALLs into 5 fish per genotype).

Cells were also transplanted into 90-day old CG1-strain syngeneic zebrafish providing a positive control for microinjection technique (i.e., the leukemias will engraft with 100% efficiency in CG1-strain fish at these cell doses) and into unmatched, wild-type strain zebrafish where engraftment is not expected. 90-day old fish are adults and were chosen because they are large enough to transplant by IP injection yet small enough to be housed en mass in sterile isolation chambers as outlined above.

Animals were examined for fluorescent leukemia growth using epi-fluorescent macroscopic observation at 10, 20, 30, and 45 days post-transplant [35, 36, 38, 68, 79, 80]. Successful engraftment was defined by long-term growth past 30 days. If leukemia cells fail to engraft or regress following engraftment, then the model is not suitably immune competent to permit long-term engraftment.

Heterozygous mutant zebrafish deficient in rag2 and jak3 were incrossed and the resultant progeny raised to 3-4 months of age. dsRED-fluorescent T-ALL were isolated from diseased fish and transplanted into incrossed animals ($1 \times 10^5$ cells, FIG. 8). Fish were then raised under normal laboratory conditions (non-GF). This unbiased analysis allowed the direct assessment of genotype-dictated engraftment potential. Homozygous rag2-deficient zebrafish (rag−/−, line #14) robustly engrafted T-ALL for >35d post-transplantation (n=2 of 2, FIG. 8) but not wild-type (n=7) or heterozygous siblings (n=9). T-ALL could also engraft into jak3 heterozygous (jak3+/−, n=7 of 7) and homozygous mutant zebrafish (jak3−/−, n=3 of 3, line #7.8) by 10-days post-transplant, but not wild-type fish (n=3). Following fin clip at 10 days post-transplant, all homozygous jak3-deficient fish died, while jak3 heterozygous and wild-type fish lived. Remarkably, by 45 days post-transplant only a subset of jak3 heterozygous fish retained T-ALL (n=2 of 7), suggesting that jak3 truncations lead to partial loss-of-function phenotypes and only partial immune competence. rag2-deficient zebrafish also facilitated robust engraftment of fluorescently-labeled zebrafish embryonal rhabdomyosaroma and melanoma (FIG. 9). In total, these experiments show that mutant lines are immune compromised, can engraft a wide range of tumors, and are viable as adults following transplant.

Example 3. Limiting Dilution Cell Transplantation of Fluorescently-Labeled T-ALL to Quantitatively Assess which Models are Best for Cell Transplantation Models that engender long-term engraftment are assessed for the ability to accurately quantify leukemia propagating cell (LPC) frequency as determined by limiting dilution cell transplantation of fluorescent-labeled T-ALL cells. This approach is a good surrogate for assessing the immune competency of each mutant line. Similar approaches have been utilized to transplant human melanomas into mice and uncovered that NOD/SCID models do not accurately quantify tumor propagating cell potential whereas NOD/SCID/Il2rg-null animals have vastly increased propensity for engraftment, likely due to profound reduction of NK cell function.

These experiments utilize fluorescent-labeled T-ALL from syngeneic CG1-strain zebrafish that have reproducible LPC frequencies of 1 in 100 [38]. As outlined above, leukemic cells are harvested from antibiotic treated fish under sterile conditions and then purified by Ficoll gradient to eliminate bacteria and fungus. Cells are stained with propidium iodide and sorted based on PI and fluorescent-protein expression into 96 well plates supplemented with $2\times10^4$ carrier blood cells isolated from microbiologically sterile, CG1-strain fish. Cells are injected into the peritoneum of 60-day old, non-irradiated recipient animals. In total, $1\times10^3$, $1\times10^2$, and 10 sorted GFP+ cells will be transferred into 5 animals at each dose. Cells are also transplanted into 60-day old CG1-strain syngeneic zebrafish providing a positive control for microinjection technique and to validate LPC frequencies for each leukemia assessed. In total, three T-ALLs will be assessed in this sub aim. Recipient fish are raised in the presence of antibiotics in sterile containment flasks as previously described [75]. Animals are examined for fluorescent leukemia growth at 10, 20, 30, 45, 60, and 90 days post-transplantation [35, 36, 38, 68, 79, 80].

Models that exhibit similar leukemia-propagating cell frequencies as implantation into CG1-strain fish are fully-immune competent. A schematic outlining these experiments is shown in FIG. 10.

Example 4. Engraftment of Regenerative Muscle Stem Cells

Optimized methods for cell transplantation of fluorescent muscle cells into irradiated recipient fish are known [82] and accomplish short-term engraftment of muscle fibers for up to 20 days. Using these muscle stem cell transplant methods to assess engraftment of regenerative cell types, muscle cells were isolated from 20-30 normal adult ubiqitin-GFP and alpha-actin-RFP transgenic fish utilizing the sterile techniques outlined above. $5\times10^4$ cells were implanted into the dorsal musculature of 90-day-old rag2-/- fish. Cells were also transplanted into wild-type sibling fish at 90-days of age. Animals were examined for fluorescent muscle engraftment for 30-45 days [75]. A schematic outlining experiments is shown in FIG. 12A.

The rag2-deficient zebrafish (line 14) were assessed for the ability to engraft muscle cells into the dorsal musculature as outlined above. rag2 homozygous mutant animals engraft muscle cells from ubiquitin-GFP+ and alpha-actin-RFP muscle robustly (n=8 of 8, $5\times10^4$ cells/fish) while rag2 heterozygous (n=4) and wild-type sibling fish (n=10) do not. Ubiquitin-GFP transgenic zebrafish exhibit robust GFP expression in most tissues, including skeletal muscle. No fish died during these 45 day transplant experiments, indicating that rag2-deficient fish are viable and can be maintained following genotyping and transplant engraftment.

These experiments are repeated in foxn1-/- and jak3-/- single mutant fish, and compound mutants for rag2-/-, jak3-/-; rag2-/-, Il2rga-/-, Il2rgb-/-; prkdc-/-, jak3-/-; and prkdc-/-, Il2rga-/-, Il2rgb-/-. These experiments will assess which models best facilitate engraftment of normal tissue-restricted, zebrafish stem cells.

Example 5. Engraftment of Zebrafish Hematopoietic Stem Cells (HSCs)

Short-term reconstitution of the immune system can be visualized in irradiated Casper fish; however, like T-ALL, a majority of animals that engraft fluorescent-labeled blood cells from marrow exhibit ablation of engrafted cells by 20 days due to recovery of the immune system and attack by host immune cells (FIG. 2) [39]. To assess the utility of our mutant fish lines for blood cell transplantation, GFP+ cells were isolated from the marrow of 30-50 normal adult ubiquitin-GFP transgenic zebrafish using sterile technique [83]. $1\times10^6$ whole kidney marrow cells were transplanted into each animal by microinjection into the peritoneal cavity (n=5 fish/genotype). The kidney marrow is the site of hematopoiesis in zebrafish and contains the HSCs. Importantly, engraftment of HSCs requires clearing of the niche; thus, transplant recipient fish will be irradiated 2 days prior to transplant with 10 gy from a Cs137 source. Transplant animals were examined for fluorescent blood cell engraftment based on distribution of GFP+ cells in the thymus, kidney, and circulation of the tail at 10, 20, 30, and 45 days post-injection. Fish were sacrificed after 45-days post-transplantation and GFP+ cells isolated from the kidney marrow to verify long-term engraftment of all cell lineages based on FACS. Morphological analysis of sorted GFP+ cells was assessed by cytospin and Wright-Giemsa/May-Grunwald staining (FIGS. 13C,F, I). Successful engraftment was defined by long-term and sustained GFP-positivity in all blood cell lineages. Loss of GFP+ cells in the blood would denote rejection and lack of immune competency within a given model.

Homozygous rag2 mutant zebrafish robustly engrafted HSCs from the whole-kidney marrow of ubiquitin-GFP transgenic fish at 45d post-transplant (FIG. 13, $1\times10^6$ cells/fish). Circulating GFP+ cells were easily visualized by whole animal imaging of rag2 mutant fish (n=8, FIG. 13G and time-lapse imaging of the tail fin). FACs showed that 30-40.7% of the marrow was replaced by donor cells (representative animal shown, FIG. 13H). Cytospins and staining of FACs sorted GFP+ cells confirmed multilineage engraftment of red blood cells, lymphocytes, and myeloid cell types (FIG. 13I). By contrast, heterozygous mutant (n=4) and wild-type fish (n=9) could not engraft GFP+ cells following sub-lethal irradiation with 10Gy (FIG. 13D-F).

These experiments are repeated in foxn1−/− and jak3−/− single mutant fish, and compound mutants for rag2−/−, jak3−/−; rag2−/−, Il2rga−/−, Il2rgb−/−; prkdc−/−, jak3−/−; and prkdc−/−, Il2rga−/−, Il2rgb−/−. These experiments will be completed in triplicate and will utilize 135 recipient fish (FIG. 12B).

Example 6. Engraftment of Human and Mouse Cancer Cells into Immune Compromised Zebrafish Cell transplantation studies using malignant cells from mouse and human were also performed; these experiments are interesting in part because the same immune responses govern rejection of cancer cells as normal cells.

Specifically, lenti-viral GFP+ or RFP+ tumor cell lines were generated or obtained to directly visualize tumor cell engraftment as outlined above.

Transplant recipient fish are raised within sterile cages and the temperature increased over 1 week ending at 35° C. Fish are acclimated to the highest temperatures for 5 days prior to engraftment with human and mouse cells. Sterile human and mouse cells are implanted into the peritoneum of 90-day-old 1) foxn1−/−, 2) rag2−/−, 3) jak3−/− single mutant fish, and compound mutants for 4) rag2−/−, jak3−/−; 5) rag2−/−, Il2rga−/−, Il2rgb−/−; 6) prkdc−/−, jak3−/−; and 7) prkdc−/−, Il2rga−/−, Il2rgb−/− ($1 \times 10^6$ cells/animal, n=5 fish/genotype). Cells are also transplanted into irradiated and non-irradiated Casper fish as a positive and negative control for microinjection, respectively. Transplant animals are raised within individual sterile 1 L flasks at 35° C. Animals will be raised in sterile conditions where partial media changes will be performed manually 2-3 times per week, and sterility tests performed using established techniques as outlined above [75]. Recipient animals are examined for fluorescent cancer cell engraftment at 10, 20, 30, and 45 days post-transplantation. Experiments are completed in triplicate.

Wild-type (n=25) and homozygous rag2-deficient fish (n=10) were successfully reared at 35° C. for >40 days showing that the fish can survive at this temperature.

Initial experiments utilized zebrafish tumor cells that engrafted robustly into the rag2−/− fish, including dsRED-labeled Myc-induced T-ALL arising in TuAB strain fish, zsYellow-labeled T-ALL arising in syngeneic CG1-strain fish, GFP-labeled kRASG12D-induced embryonal rhabdomyosarcoma (ERMS) arising in CG1-strain fish, and melanomas arising in p53-deficient nacre strain fish injected with transgenes that overexpress mitfa and BRAFV600E. See FIGS. 15A-T. Moreover, human MM383 melanoma cells can be engrafted into homozygous mutant fish (n=4 of 9) but not wild-type or heterozygous siblings (n=9); FIGS. 14A-C. These experiments show that a subset of rag2-deficient zebrafish can successfully engraft human tumors at 35° C. Jak3 mutant lines also engraft zebrafish tissue and tumor, and so are also useful in engraftment studies.

Additional experiments utilize the following human cell lines: 1) human RD and SMS-CTR cell lines (embryonal rhabdomyosarcoma), 2) panc1 cells (pancreatic adenocarcinoma), 3) HCT 116 (colorectal carcinoma), 4) C8161 or MM383 (melanoma), 5) MOLT16 (T-ALL), or 6) KG-1 (AML). Each of these cell lines is available in the lab or from ATTC. Each cell line is assessed for continued growth at 35° C. prior to use in cell transplantation experiments. Mouse tumor cells are also assessed for engraftment including: 1) Notch over-expressing T-ALLs induced in PTEN-deficient mice, and 2) U57810 mouse primary Myf6cre-derived ERMS with p53 loss. Each of these has been shown to reconstitute disease when transplanted into syngeneic and immune suppressed mice, respectively. Cells are implanted into the peritoneal cavity of recipient fish (5 microliter volume, $1 \times 10^6$ cells/fish).

REFERENCES

1. Barberi, T., et al., Derivation of engraftable skeletal myoblasts from human embryonic stem cells. Nat Med, 2007. 13(5): p. 642-8.
2. Cooper, R. N., et al., A new immunodeficient mouse model for human myoblast transplantation. Hum Gene Ther, 2001. 12(7): p. 823-31.
3. Ehrhardt, J., et al., Human muscle precursor cells give rise to functional satellite cells in vivo. Neuromuscul Disord, 2007. 17(8): p. 631-8.
4. Huard, J., et al., High efficiency of muscle regeneration after human myoblast clone transplantation in SCID mice. J Clin Invest, 1994. 93(2): p. 586-99.
5. Negroni, E., et al., In vivo myogenic potential of human CD133+ muscle-derived stem cells: a quantitative study. Mol Ther, 2009. 17(10): p. 1771-8.
6. Dick, J. E., et al., In vivo dynamics of human stem cell repopulation in NOD/SCID mice. Ann N Y Acad Sci, 2001. 938: p. 184-90.
7. Guenechea, G., et al., Distinct classes of human stem cells that differ in proliferative and self-renewal potential. Nat Immunol, 2001. 2(1): p. 75-82.
8. Majeti, R., C. Y. Park, and I. L. Weissman, Identification of a hierarchy of multipotent hematopoietic progenitors in human cord blood. Cell Stem Cell, 2007. 1(6): p. 635-45.
9. McDermott, S. P., et al., Comparison of human cord blood engraftment between immunocompromised mouse strains. Blood, 2010. 116(2): p. 193-200.
10. Notta, F., et al., Isolation of single human hematopoietic stem cells capable of long-term multilineage engraftment. Science, 2011. 333(6039): p. 218-21.
11. Park, C. Y., R. Majeti, and I. L. Weissman, In vivo evaluation of human hematopoiesis through xenotransplantation of purified hematopoietic stem cells from umbilical cord blood. Nat Protoc, 2008. 3(12): p. 1932-40.
12. Tanaka, S., et al., Development of mature and functional human myeloid subsets in hematopoietic stem cell-engrafted NOD/SCID/IL2rgammaKO mice. J Immunol, 2012. 188(12): p. 6145-55.
13. Racki, W. J., et al., NOD-scid IL2rgamma(null) mouse model of human skin transplantation and allograft rejection. Transplantation, 2010. 89(5): p. 527-36.
14. van Laake, L. W., et al., Human embryonic stem cell-derived cardiomyocytes survive and mature in the mouse heart and transiently improve function after myocardial infarction. Stem Cell Res, 2007. 1(1): p. 9-24.
15. Kroon, E., et al., Pancreatic endoderm derived from human embryonic stem cells generates glucose-responsive insulin-secreting cells in vivo. Nat Biotechnol, 2008. 26(4): p. 443-52.
16. Cheng, X., et al., Self-renewing endodermal progenitor lines generated from human pluripotent stem cells. Cell Stem Cell, 2012. 10(4): p. 371-84.
17. Yui, S., et al., Functional engraftment of colon epithelium expanded in vitro from a single adult Lgr5(+) stem cell. Nat Med, 2012. 18(4): p. 618-23.

18. Nehls, M., et al., New member of the winged-helix protein family disrupted in mouse and rat nude mutations. Nature, 1994. 372(6501): p. 103-7.
19. Bosma, G. C., R. P. Custer, and M. J. Bosma, A severe combined immunodeficiency mutation in the mouse. Nature, 1983. 301(5900): p. 527-30.
20. Blunt, T., et al., Defective DNA-dependent protein kinase activity is linked to V(D)J recombination and DNA repair defects associated with the murine scid mutation. Cell, 1995. 80(5): p. 813-23.
21. Shultz, L. D., et al., Multiple defects in innate and adaptive immunologic function in NOD/LtSz-scid mice. J Immunol, 1995. 154(1): p. 180-91.
22. Mombaerts, P., et al., RAG-1-deficient mice have no mature B and T lymphocytes. Cell, 1992. 68(5): p. 869-77.
23. Shultz, L. D., et al., NOD/LtSz-Rag1null mice: an immunodeficient and radioresistant model for engraftment of human hematolymphoid cells, HIV infection, and adoptive transfer of NOD mouse diabetogenic T cells. J Immunol, 2000. 164(5): p. 2496-507.
24. Pearson, T., et al., Non-obese diabetic-recombination activating gene-1 (NOD-Rag1 null) interleukin (IL)-2 receptor common gamma chain (IL2r gamma null) null mice: a radioresistant model for human lymphohaematopoietic engraftment. Clin Exp Immunol, 2008. 154 (2): p. 270-84.
25. Ishikawa, F., et al., Development of functional human blood and immune systems in NOD/SCID/IL2 receptor {gamma} chain(null) mice. Blood, 2005. 106(5): p. 1565-73.
26. Shultz, L. D., et al., Human lymphoid and myeloid cell development in NOD/LtSz-scid IL2R gamma null mice engrafted with mobilized human hemopoietic stem cells. J Immunol, 2005. 174(10): p. 6477-89.
27. Shultz, L. D., et al., NOD/LtSz-Rag1nullPfpnull mice: a new model system with increased levels of human peripheral leukocyte and hematopoietic stem-cell engraftment. Transplantation, 2003. 76(7): p. 1036-42.
28. Christianson, S. W., et al., Enhanced human CD4+ T cell engraftment in beta2-microglobulin-deficient NOD-scid mice. J Immunol, 1997. 158(8): p. 3578-86.
29. Nosaka, T., et al., Defective lymphoid development in mice lacking Jak3. Science, 1995. 270(5237): p. 800-2.
30. Thomis, D. C., et al., Defects in B lymphocyte maturation and T lymphocyte activation in mice lacking Jak3. Science, 1995. 270(5237): p. 794-7.
31. Boehm, T., C. C. Bleul, and M. Schorpp, Genetic dissection of thymus development in mouse and zebrafish. Immunol Rev, 2003. 195: p. 15-27.
32. Iwanami, N., et al., Genetic evidence for an evolutionarily conserved role of IL-7 signaling in T cell development of zebrafish. J Immunol, 2011. 186(12): p. 7060-6.
33. Wienholds, E., et al., Target-selected inactivation of the zebrafish rag1 gene. Science, 2002. 297(5578): p. 99-102.
34. White, R. M., et al., Transparent adult zebrafish as a tool for in vivo transplantation analysis. Cell Stem Cell, 2008. 2(2): p. 183-9.
35. Blackburn, J. S., S. Liu, and D. M. Langenau, Quantifying the Frequency of Tumor-propagating Cells Using Limiting Dilution Cell Transplantation in Syngeneic Zebrafish. J Vis Exp, 2011(53).
36. Blackburn, J. S., et al., Notch signaling expands a pre-malignant pool of T-cell acute lymphoblastic leukemia clones without affecting leukemia-propagating cell frequency. Leukemia, 2012.
37. Ignatius, M. S., et al., In Vivo imaging of tumor-propagating cells, regional tumor heterogeneity, and dynamic cell movements in embryonal rhabdomyosarcoma. Cancer Cell, 2012. 21(5): p. 680-93.
38. Smith, A. C., et al., High-throughput cell transplantation establishes that tumor-initiating cells are abundant in zebrafish T-cell acute lymphoblastic leukemia. Blood, 2010.
39. Traver, D., et al., Effects of lethal irradiation in zebrafish and rescue by hematopoietic cell transplantation. Blood, 2004. 104(5): p. 1298-305.
40. Hansen, J. D. and A. G. Zapata, Lymphocyte development in fish and amphibians. Immunological Reviews, 1998. 166: p. 199-220.
41. Willett, C. E., et al., Early hematopoiesis and developing lymphoid organs in the zebrafish. Developmental Dynamics, 1999. 214(4): p. 323-36.
42. Willett, C. E., et al., Expression of zebrafish rag genes during early development identifies the thymus. Developmental Biology, 1997. 182(2): p. 331-41.
43. Langenau, D. M., et al., In vivo tracking of T cell development, ablation, and engraftment in transgenic zebrafish. Proceedings of the National Academy of Sciences of the United States of America, 2004. 101(19): p. 7369-74.
44. Trede, N. S., et al., The use of zebrafish to understand immunity. Immunity, 2004. 20(4): p. 367-79.
45. Haldi, M., et al., Human melanoma cells transplanted into zebrafish proliferate, migrate, produce melanin, form masses and stimulate angiogenesis in zebrafish. Angiogenesis, 2006. 9(3): p. 139-51.
46. Lee, L. M., et al., The fate of human malignant melanoma cells transplanted into zebrafish embryos: assessment of migration and cell division in the absence of tumor formation. Dev Dyn, 2005. 233(4): p. 1560-70.
47. Ghotra, V. P., et al., Automated whole animal bio-imaging assay for human cancer dissemination. PLoS One, 2012. 7(2): p. e31281.
48. Ali, S., et al., Zebrafish embryos and larvae: a new generation of disease models and drug screens. Birth Defects Res C Embryo Today, 2011. 93(2): p. 115-33.
49. Konantz, M., et al., Zebrafish xenografts as a tool for in vivo studies on human cancer. Ann N Y Acad Sci, 2012. 1266(1): p. 124-137.
50. Corkery, D. P., G. Dellaire, and J. N. Berman, Leukaemia xenotransplantation in zebrafish—chemotherapy response assay in vivo. Br J Haematol, 2011. 153(6): p. 786-9.
51. Traver, D., et al., Transplantation and in vivo imaging of multilineage engraftment in zebrafish bloodless mutants. Nature Immunology, 2003. 4(12): p. 1238-1246.
52. Hess, I., et al., Zebrafish model for allogeneic hematopoietic cell transplantation not requiring preconditioning. Proc Natl Acad Sci USA, 2013. 110(11): p. 4327-32.
53. Stoletov, K., et al., High-resolution imaging of the dynamic tumor cell vascular interface in transparent zebrafish. Proc Natl Acad Sci USA, 2007. 104(44): p. 17406-11.
54. Doyon, Y., et al., Heritable targeted gene disruption in zebrafish using designed zinc-finger nucleases. Nat Biotechnol, 2008. 26(6): p. 702-8.
55. Foley, J. E., et al., Targeted mutagenesis in zebrafish using customized zinc-finger nucleases. Nat Protoc, 2009. 4(12): p. 1855-67.

56. Foley, J. E., et al., Rapid mutation of endogenous zebrafish genes using zinc finger nucleases made by Oligomerized Pool ENgineering (OPEN). PLoS One, 2009. 4(2): p. e4348.
57. Meng, X., et al., Targeted gene inactivation in zebrafish using engineered zinc-finger nucleases. Nat Biotechnol, 2008. 26(6): p. 695-701.
58. Sander, J. D., et al., Selection-free zinc-finger-nuclease engineering by context-dependent assembly (CoDA). Nat Methods, 2011. 8(1): p. 67-9.
59. Sander, J. D., et al., Engineering zinc finger nucleases for targeted mutagenesis of zebrafish. Methods Cell Biol, 2011. 104: p. 51-8.
60. Zhu, C., et al., Evaluation and application of modularly assembled zinc-finger nucleases in zebrafish. Development, 2011. 138(20): p. 4555-64.
61. Cade, L., et al., Highly efficient generation of heritable zebrafish gene mutations using homo- and heterodimeric TALENs. Nucleic Acids Res, 2012.
62. Dahlem, T. J., et al., Simple Methods for Generating and Detecting Locus-Specific Mutations Induced with TALENs in the Zebrafish Genome. PLoS Genet, 2012. 8(8): p. e1002861.
63. Huang, P., et al., Heritable gene targeting in zebrafish using customized TALENs. Nat Biotechnol, 2011. 29(8): p. 699-700.
64. Moore, F. E., et al., Improved Somatic Mutagenesis in Zebrafish Using Transcription Activator-Like Effector Nucleases (TALENs). PLoS One, 2012. 7(5): p. e37877.
65. Sander, J. D., et al., Targeted gene disruption in somatic zebrafish cells using engineered TALENs. Nat Biotechnol, 2011. 29(8): p. 697-8.
66. Cifuentes, D., et al., A novel miRNA processing pathway independent of Dicer requires Argonaute2 catalytic activity. Science, 2010. 328(5986): p. 1694-8.
67. Siekmann, A. F., et al., Chemokine signaling guides regional patterning of the first embryonic artery. Genes Dev, 2009. 23(19): p. 2272-7.
68. Blackburn, J. S., et al., High-throughput imaging of adult fluorescent zebrafish with an LED fluorescence macroscope. Nat Protoc, 2011. 6(2): p. 229-41.
69. Macchi, P., et al., Mutations of Jak-3 gene in patients with autosomal severe combined immune deficiency (SCID). Nature, 1995. 377(6544): p. 65-8.
70. Russell, S. M., et al., Mutation of Jak3 in a patient with SCID: essential role of Jak3 in lymphoid development. Science, 1995. 270(5237): p. 797-800.
71. Frank, J., et al., Exposing the human nude phenotype. Nature, 1999. 398(6727): p. 473-4.
72. Noguchi, M., et al., Interleukin-2 receptor gamma chain mutation results in X-linked severe combined immunodeficiency in humans. Cell, 1993. 73(1): p. 147-57.
73. Perryman, L. E., Molecular pathology of severe combined immunodeficiency in mice, horses, and dogs. Vet Pathol, 2004. 41(2): p. 95-100.
74. Ding, Q., et al., DNA-PKcs mutations in dogs and horses: allele frequency and association with neoplasia. Gene, 2002. 283(1-2): p. 263-9.
75. Pham, L. N., et al., Methods for generating and colonizing gnotobiotic zebrafish. Nat Protoc, 2008. 3(12): p. 1862-75.
76. Rawls, J. F., B. S. Samuel, and J. I. Gordon, Gnotobiotic zebrafish reveal evolutionarily conserved responses to the gut microbiota. Proc Natl Acad Sci USA, 2004. 101(13): p. 4596-601.
77. Rawls, J. F., et al., Reciprocal gut microbiota transplants from zebrafish and mice to germ-free recipients reveal host habitat selection. Cell, 2006. 127(2): p. 423-33.
78. Langenau, D. M., et al., Cre/lox-regulated transgenic zebrafish model with conditional myc-induced T cell acute lymphoblastic leukemia. Proc Natl Acad Sci USA, 2005. 102(17): p. 6068-73.
79. Langenau, D. M., et al., Myc-induced T cell leukemia in transgenic zebrafish. Science, 2003. 299(5608): p. 887-90.
80. Langenau, D. M., et al., Co-injection strategies to modify radiation sensitivity and tumor initiation in transgenic Zebrafish. Oncogene, 2008. 27(30): p. 4242-8.
81. Alexander, M. S., et al., Isolation and transcriptome analysis of adult zebrafish cells enriched for skeletal muscle progenitors. Muscle Nerve, 2011. 43(5): p. 741-50.
82. Higashijima, S., et al., High-frequency generation of transgenic zebrafish which reliably express GFP in whole muscles or the whole body by using promoters of zebrafish origin. Dev Biol, 1997. 192(2): p. 289-99.
83. Mosimann, C., et al., Ubiquitous transgene expression and Cre-based recombination driven by the ubiquitin promoter in zebrafish. Development, 2011. 138(1): p. 169-77.
84. Langenau, D. M., et al., Effects of RAS on the genesis of embryonal rhabdomyosarcoma. Genes Dev, 2007. 21(11): p. 1382-95.
85. Leong, I. U. S. et al., Targeted Mutagenesis of Zebrafish: Use of Zinc Finger Nucleases. Birth Defects Research (Part C) 93:249-255 (2011).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A genetically-modified fish comprising engineered or induced homozygous genetic alterations in prkdc and Il2rga;
   wherein the genetic alterations result in an inactivation of both alleles of the prkdc and Il2rga genes,
   wherein the fish are immune compromised and can be engrafted with exogenous cells without having the exogenous cells rejected, and
   wherein the fish are viable.

2. A method of engrafting a mammalian cell, the method comprising transplanting a mammalian cell into the genetically-modified fish of claim 1 and maintaining the genetically-modified fish under conditions that allow the fish and the cell to survive.

3. The method of claim 2, wherein the cells are tumor cells.

4. The method of claim 2, wherein the cells are stem cells or progeny of differentiated stem cells.

5. A method of identifying a candidate therapeutic compound for the treatment of a mammalian tumor, the method comprising:
   transplanting cells from a mammalian tumor into a genetically-modified fish of claim 1;
   contacting the fish with a test compound;
   evaluating the growth of a tumor comprising the mammalian tumor cells in the presence of the test compound; comparing the level of growth of the tumor in the presence of the test compound to that in the presence of a control substance; and identifying a compound that decreases the level of growth of the mammalian tumor cells as a candidate therapeutic compound.

6. The genetically-modified fish of claim 1, wherein the genetic alteration is a frameshift mutation.

7. The genetically-modified fish of claim 1, wherein the exogenous cells are fish cells or mammalian cells.

8. The genetically-modified fish of claim 7, wherein the exogenous cells are mammalian cells, and the mammalian cells are human cells.

9. The genetically-modified fish of claim 1, wherein the exogenous cells are cancer cells.

10. A method of engrafting a zebrafish cell, the method comprising transplanting a zebrafish cell into the genetically-modified fish of claim 1 and maintaining the genetically-modified fish under conditions that allow the fish and the cell to survive.

11. The method of claim 10, wherein the zebrafish cells are stem cells.

12. The method of claim 10, wherein the zebrafish cells are cancer cells.

* * * * *